United States Patent
Furuya et al.

(10) Patent No.: US 12,384,870 B2
(45) Date of Patent: *Aug. 12, 2025

(54) METHOD FOR SETTING POLYMERIZATION CONDITION AND METHOD FOR MANUFACTURING OPTICAL MATERIAL

(71) Applicant: MITSUI CHEMICALS, INC., Tokyo (JP)

(72) Inventors: Masayuki Furuya, Arao (JP); Takeshi Nishimura, Yanagawa (JP); Shinsuke Ito, Omuta (JP); Tatsuya Ogawa, Omuta (JP)

(73) Assignee: MITSUI CHEMICALS, INC., Tokyo (JP)

( * ) Notice: Subject to any disclaimer, the term of this patent is extended or adjusted under 35 U.S.C. 154(b) by 1022 days.

This patent is subject to a terminal disclaimer.

(21) Appl. No.: 17/040,136

(22) PCT Filed: Jun. 6, 2018

(86) PCT No.: PCT/JP2018/021769
§ 371 (c)(1),
(2) Date: Sep. 22, 2020

(87) PCT Pub. No.: WO2019/187176
PCT Pub. Date: Oct. 3, 2019

(65) Prior Publication Data
US 2021/0079151 A1    Mar. 18, 2021

(30) Foreign Application Priority Data

Mar. 27, 2018   (JP) ................... 2018-059326

(51) Int. Cl.
| | |
|---|---|
| C08G 18/64 | (2006.01) |
| C08F 18/24 | (2006.01) |
| C08G 18/72 | (2006.01) |
| C08G 75/08 | (2006.01) |
| G01N 3/54 | (2006.01) |
| G16C 20/40 | (2019.01) |

(52) U.S. Cl.
CPC .......... C08G 18/6453 (2013.01); C08F 18/24 (2013.01); C08G 18/72 (2013.01); C08G 75/08 (2013.01); G01N 3/54 (2013.01); G16C 20/40 (2019.02)

(58) Field of Classification Search
CPC .... C08G 18/6453; C08G 18/72; C08G 75/08; C08G 18/758; C08G 18/242; C08G 18/3876; C08G 18/7642; C08G 18/16; C08F 18/24; C08F 2/48; C08F 2/50; C08F 218/24; C08F 20/10; C08F 22/04; G01N 3/54; G16C 20/40; G16C 20/10; G16C 20/30; G16C 60/00; B29C 39/006; B29C 39/38; B29C 39/44; G02B 1/041

See application file for complete search history.

(56) References Cited

U.S. PATENT DOCUMENTS

| | | |
|---|---|---|
| 8,044,165 B2 | 10/2011 | Kawaguchi et al. |
| 8,586,695 B2 | 11/2013 | Kawato et al. |
| 2010/0010192 A1* | 1/2010 | Kawaguchi ........ C08G 18/3876 528/374 |
| 2010/0029890 A1 | 2/2010 | Kawato et al. |
| 2010/0209307 A1* | 8/2010 | Drabish ................. G16C 20/30 703/2 |
| 2011/0065884 A1 | 3/2011 | Kawato et al. |
| 2015/0293265 A1 | 10/2015 | Kawato et al. |

(Continued)

FOREIGN PATENT DOCUMENTS

| | | |
|---|---|---|
| JP | 2001106703 A | 4/2001 |
| JP | 2003252910 A | 9/2003 |
| JP | 2004091688 A | 3/2004 |

(Continued)

OTHER PUBLICATIONS

Heidarian, Javad, Nayef Mohd Ghasem, and Wan Mohd Ashri Wan Daud. "Study on kinetics of polymerization of dimer fatty acids with ethylenediamine in the presence of catalyst." Chemical Engineering Journal 100.1-3 (2004): 85-93.*

International Search Report (PCT/ISA/210) issued on Sep. 11, 2018, by the Japanese Patent Office as the International Searching Authority for International Application No. PCT/JP2018/021769.

Written Opinion (PCT/ISA/237) issued on Sep. 11, 2018, by the Japanese Patent Office as the International Searching Authority for International Application No. PCT/JP2018/021769.

(Continued)

*Primary Examiner* — G. Steven Vanni
(74) *Attorney, Agent, or Firm* — BUCHANAN INGERSOLL & ROONEY PC

(57) ABSTRACT

A method for setting polymerization condition includes a physical property acquiring step of, when heating a composition including a polymerization-reactive compound and a polymerization catalyst and/or a polymerization initiator and retaining heat at a predetermined temperature, acquiring a physical property value a derived from a functional group before heating of the polymerization-reactive compound and a physical property value b derived from a remaining functional group after maintaining a temperature for a predetermined time; a remaining functional group ratio calculating step of calculating a remaining functional group ratio from the physical property value a and the physical property value b; a reaction rate coefficient calculating step of calculating a reaction rate coefficient from the remaining functional group ratio on the basis of a reaction rate equation; and a polymerization temperature calculating step of calculating a polymerization temperature on the basis of the reaction rate coefficient and conditions below.

11 Claims, 6 Drawing Sheets

(56) References Cited

U.S. PATENT DOCUMENTS

2017/0212054 A1* 7/2017 Reed .................. B01J 8/1809
2019/0153131 A1* 5/2019 Ogawa .................. G02C 7/10

FOREIGN PATENT DOCUMENTS

| JP | 2009226742 A | 10/2009 |
| JP | 2012240414 A | 12/2012 |
| KR | 10-2015-0070233 A | 6/2015 |
| WO | 2008035457 A1 | 3/2008 |
| WO | 2008047626 A1 | 4/2008 |

OTHER PUBLICATIONS

Kang, S. C., et al., "Kinetics of Acrylamide Solution Polymerization Using Potassium Persulfate as an Initiator by in situ IR", Macromolecular Research, vol. 12, No. 1, p. 107-111, (2004). (Cited in Office Action dated Dec. 1, 2021, for Korean Application No. 10-2020-7027951).

* cited by examiner

METHOD FOR SETTING POLYMERIZATION CONDITION AND METHOD FOR MANUFACTURING OPTICAL MATERIAL

TECHNICAL FIELD

The present invention relates to a method for setting polymerization condition and a method for manufacturing an optical material having an excellent appearance.

BACKGROUND ART

Plastic lenses are lighter and harder to break than inorganic lenses and are able to be dyed and have thus rapidly become widespread as optical materials for spectacle lenses and camera lenses and the like. So far, various molded articles for lenses have been developed and used.

Among these, typical examples include an allyl resin obtained from diethylene glycol bisallyl carbonate and diallyl isophthalate, a (meth)acrylic resin obtained from (meth)acrylate, a polythiourethane resin obtained from isocyanate and thiol, and the like.

Patent Document 1 proposes, as a method for manufacturing a thick plastic lens having a high refractive index, a manufacturing method provided with a holding step of filling a polymerizable composition into a mold and then maintaining the polymerizable composition at an initial temperature or higher at the time of filling, and a cooling step of cooling the polymerizable composition.

Patent Document 2 discloses, as a method for manufacturing a plastic lens, a manufacturing method in which a curing step is provided with a filling step, then a holding step of maintaining a polymerizable composition at an initial temperature or higher at the time of the filling step, and, after the holding step, a cooling step of cooling the polymerizable composition.

RELATED DOCUMENTS

Patent Documents

[Patent Document 1] JP 2012-240414 A
[Patent Document 2] JP 2009-226742 A

SUMMARY OF THE INVENTION

Technical Problem

As disclosed in Patent Document 1 or Patent Document 2, a plastic lens is usually formed by polymerizing and curing a polymerizable composition filled in a pair of molds; however, the polymerization rate of the polymerizable composition changes depending on the temperature and a slight temperature distribution locally increases or decreases the polymerization rate.

For this reason, for example, a portion where the polymerization rate is increased has a higher molecular weight than others and precipitates downward or rises upward. In addition, in the mold, convention currents of the polymerizable composition may be generated. And then, when the polymerizable composition is cured while traces thereof remain, there is a concern that optical distortion or striae may be generated in the plastic lens.

The polymerization temperature condition is an extremely important condition for suppressing optical distortion and striae. So far, examples of polymerization temperature conditions include the conditions disclosed in Patent Document 1 or Patent Document 2; however, setting the temperature conditions according to kinetic analysis of the polymerizable composition has not yet been performed.

An object of the present invention is to set a polymerization temperature condition under which optical distortion or striae accompanying curing of a polymerizable composition is suppressed and an optical material having an excellent appearance is obtained.

Solution to Problem

As a result of intensive studies conducted by the present inventors, it was found that appropriately setting polymerization temperature conditions according to a predetermined analysis makes it possible to increase the polymerization ratio of the optical material and to further suppress variations in polymerization rate in the process of polymerizing and curing the optical material and, as a result, the generation of optical distortion and striae is suppressed and it is possible to obtain an optical material having an excellent appearance, thereby completing the present invention.

That is, it is possible to illustrate the present invention as follows.

[1] A method for setting polymerization condition including a physical property acquiring step of, when heating a composition including a polymerization-reactive compound and a polymerization catalyst and/or a polymerization initiator and retaining heat at a predetermined temperature, acquiring a physical property value a derived from a functional group before heating of the polymerization-reactive compound and a physical property value b derived from a remaining functional group after maintaining a temperature for a predetermined time; a remaining functional group ratio calculating step of calculating a remaining functional group ratio from the physical property value a and the physical property value b; a reaction rate coefficient calculating step of calculating a reaction rate coefficient from the remaining functional group ratio on the basis of a reaction rate equation; and a polymerization temperature calculating step of calculating a polymerization temperature on the basis of the reaction rate coefficient and conditions below.
(Conditions)
In a range of 10% or more and 80% or less of a polymerization ratio, a polymerization rate is 0.4%/hr or more and 15%/hr or less, and a standard deviation is 2.3%/hr or less

[2] The method for setting polymerization condition according to [1], in which the physical property values a and b are a heat value, a specific gravity, a weight-average molecular weight, a number-average molecular weight, a spectral intensity in IR measurement, a $^1$H-NMR spectral intensity, or a $^{13}$C-NMR spectral intensity.

[3] A method for manufacturing an optical material, including polymerizing a composition including a polymerization-reactive compound, and a polymerization catalyst and/or a polymerization initiator under conditions below.
(Conditions)
In a range of 10% or more and 80% or less of a polymerization ratio, a polymerization rate is 0.4%/hr or more and 15%/hr or less, and a standard deviation is 2.3%/hr or less.

[4] The method for manufacturing an optical material according to 3, in which polymerizing is performed under polymerization temperature conditions obtained by the method according to [1] or [2].

[5] The method for manufacturing an optical material according to [3] or [4], in which the composition includes a polyisocyanate compound and an active hydrogen compound which are the polymerization-reactive compounds, and the polymerization catalyst.

[6] The method for manufacturing an optical material according to [5], in which the polyisocyanate compound includes at least one kind selected from aliphatic polyisocyanate, aromatic polyisocyanate, heterocyclic polyisocyanate, and alicyclic polyisocyanate.

[7] The method for manufacturing an optical material according to [5] or [6], in which the active hydrogen compound includes at least one kind selected from a group consisting of a polythiol compound having two or more mercapto groups, a hydroxythiol compound having one or more mercapto groups and one or more hydroxyl groups, a polyol compound having two or more hydroxyl groups, and an amine compound.

[8] The method for manufacturing an optical material according to [3] or [4], in which the composition includes at least one kind of compounds selected from an allyl carbonate compound, a (meth)acrylate compound, and an episulfide compound, which are the polymerization-reactive compounds, and the polymerization initiator or the polymerization catalyst.

[9] The method for manufacturing an optical material according to [8], in which the allyl carbonate compound is represented by General Formula (1),

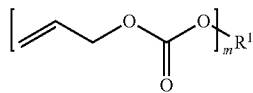

(1)

in which $R^1$ represents a chained or branched divalent to 20-valent group derived from an aliphatic polyol with 3 to 35 carbon atoms which may include a hetero atom, or a divalent to 20-valent group derived from a cycloaliphatic polyol with 5 to 40 carbon atoms which may include a hetero atom, m represents an integer of 2 to 10, and $R^1$ does not include an allyloxycarbonyl group.

[10] The method for manufacturing an optical material according to [8], in which the (meth)acrylate compound is represented by General Formula (2),

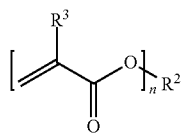

(2)

in which $R^2$ represents a divalent to tetravalent organic group with 1 to 30 carbon atoms which may include a hetero atom or an aromatic group, $R^3$ represents a hydrogen atom or a methyl group, and n represents an integer of 2 to 4.

[11] The method for manufacturing an optical material according to [8], in which the episulfide compound is represented by General Formula (3),

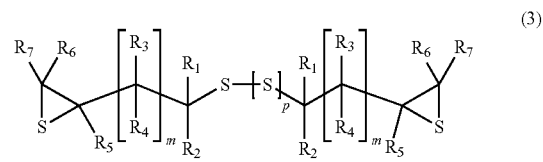

(3)

in which, in General Formula (3), $R_1$ to $R_7$ may be the same or different and represent a hydrogen atom, a linear or branched alkyl group with 1 or more and 10 or less carbon atoms, or a substituted or unsubstituted aryl group with 6 or more and 18 or less carbon atoms, m represents an integer of 0 or more and 2 or less, and p represents an integer of 0 or more and 4 or less.

[12] An apparatus for setting polymerization condition including a physical property acquiring unit for, when heating a composition including a polymerization-reactive compound, and a polymerization catalyst and/or a polymerization initiator and retaining heat at a predetermined temperature, acquiring a physical property value a derived from a functional group before heating of the polymerization-reactive compound and a physical property value b derived from a remaining functional group after maintaining a temperature for a predetermined time; a remaining functional group ratio calculating unit for calculating a remaining functional group ratio from the physical property value a and the physical property value b; a reaction rate coefficient calculating unit for calculating a reaction rate coefficient from the remaining functional group ratio on the basis of a reaction rate equation; and a polymerization temperature calculating unit for calculating a polymerization temperature on the basis of the reaction rate coefficient and conditions below (Conditions)

In a range of 10% or more and 80% or less of a polymerization ratio, a polymerization rate is 0.4%/hr or more and 15%/hr or less, and a standard deviation is 2.3%/hr or less.

[13] A computer program for setting polymerization conditions for a composition including a polymerization-reactive compound, and a polymerization catalyst and/or a polymerization initiator, the computer program causing a computer to implement functions of: a physical property acquisition unit for, when heating a composition including a polymerization-reactive compound and a polymerization catalyst and/or a polymerization initiator and retaining heat at a predetermined temperature, acquiring a physical property value a derived from a functional group before heating of the polymerization-reactive compound and a physical property value b derived from a remaining functional group after maintaining a temperature for a predetermined time; a remaining functional group ratio calculating unit for calculating a remaining functional group ratio from the physical property value a and the physical property value b; a reaction rate coefficient calculating unit for calculating a reaction rate coefficient from the remaining functional group ratio on the basis of a reaction rate equation; and a polymerization temperature calculating unit for calculating a polymerization temperature on the basis of the reaction rate coefficient and conditions below (Conditions)

In a range of 10% or more and 80% or less of a polymerization ratio, a polymerization rate is 0.4%/hr or more and 15%/hr or less, and a standard deviation is 2.3%/hr or less.

[14] An apparatus for manufacturing optical material including a heating unit for heating a composition including a polymerization-reactive compound and a polymerization catalyst and/or a polymerization initiator; the apparatus for setting polymerization condition according to [12]; and a control unit for controlling the heating unit so as to heat the composition including a polymerization-reactive compound and a polymerization catalyst and/or a polymerization initiator on the basis of polymerization temperature conditions obtained by the apparatus for setting polymerization condition.

In the present invention, the polymerization ratio [%] is a ratio of the polymerization-reactive compound which is polymerized among the polymerization-reactive compounds used. The polymerization rate [%/h] is a value obtained by dividing the polymerization ratio by time. A polymerization time is the time from the mixing of a composition formed of a combination of a polymerization-reactive compound and a polymerization catalyst and/or a polymerization initiator until the curing thereof.

Advantageous Effects of Invention

According to the method for setting polymerization condition of the present invention, it is possible to obtain polymerization temperature conditions with which the generation of optical distortion and striae is suppressed and it is possible to obtain an optical material having an excellent appearance. Furthermore, the method for manufacturing an optical material using the obtained polymerization temperature conditions makes it possible to suppress the generation of optical distortion and striae and obtain an optical material having an excellent appearance.

Moreover, according to the present invention, it is also possible to provide an apparatus for setting polymerization condition and a computer program for calculating polymerization temperature conditions, and an apparatus for manufacturing optical material provided with the apparatus for setting polymerization condition.

BRIEF DESCRIPTION OF THE DRAWINGS

The above and other objects, features and advantages will become more apparent from preferable embodiments described below and the accompanying drawings below.

DESCRIPTION OF EMBODIMENTS

Figure 1:
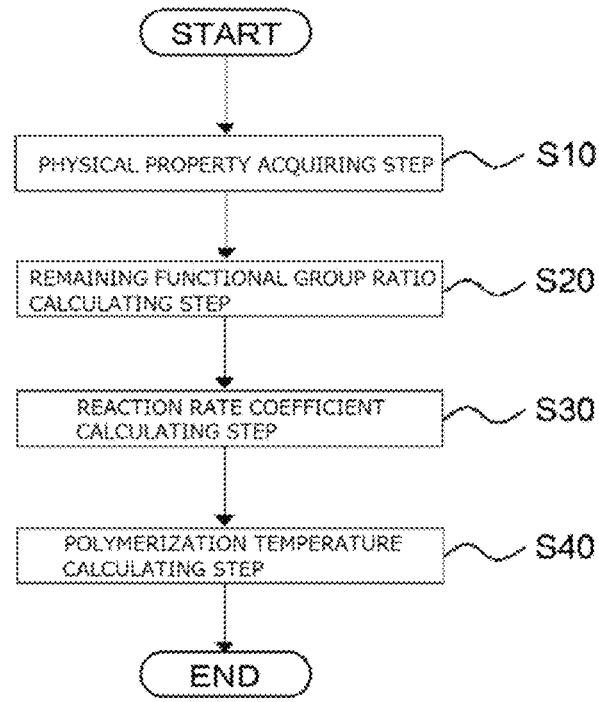
FIG. 1 is a flowchart of a method for setting polymerization condition according to the present embodiment.

A description will be given below of embodiments of the present invention using drawings. In all the drawings, the same components are denoted by the same reference numerals and description thereof will not be repeated.

In the following description, a storage unit 100, a physical property acquiring unit 120, a remaining functional group ratio calculating unit 140, a reaction rate coefficient calculating unit 160, and a polymerization temperature calculating unit 180 of an apparatus for setting polymerization condition 10 are shown as a block of functional units rather than a configuration of hardware units. The storage unit 100, the physical property acquiring unit 120, the remaining functional group ratio calculating unit 140, the reaction rate coefficient calculating unit 160, and the polymerization temperature calculating unit 180 of the apparatus for setting polymerization condition 10 are implemented by any combination of hardware and software on the basis of the CPU of any computer, a memory, a program for implementing a component of the figure loaded into a memory, a storage medium such as a hard disk for storing such a program and a network connection interface. The implementation method and apparatus may have various modifications.

FIG. 1 is a flowchart of the method for setting polymerization condition according to the present embodiment.

The method for setting polymerization condition according to the present embodiment is a method for setting polymerization temperature conditions in a composition including a polymerization-reactive compound and a polymerization catalyst and/or a polymerization initiator.

As shown in FIG. 1, the method for setting polymerization condition includes a physical property acquiring step S10, a remaining functional group ratio calculating step S20, a reaction rate coefficient calculating step S30, and a polymerization temperature calculating step S40.

In the physical property acquiring step S10, in a case of heating a composition including a polymerization-reactive compound and a polymerization catalyst and/or a polymerization initiator and retaining heat at a predetermined temperature, a physical property value a derived from a functional group before heating of the polymerization-reactive compound and a physical property value b derived from a remaining functional group after maintaining a temperature for a predetermined time are acquired. In the remaining functional group ratio calculating step S20, the remaining functional group ratio is calculated from the physical property value a and physical property value b. In the reaction rate coefficient calculating step S30, a reaction rate coefficient is calculated from the remaining functional group ratio on the basis of a reaction rate equation. In the polymerization temperature calculating step S40, a polymerization temperature is calculated on the basis of the reaction rate coefficient and conditions below.

Conditions: In a range of polymerization ratio of 10% or more and 80% or less, the polymerization rate is 0.4%/hr or more and 15%/hr or less and the standard deviation of the polymerization rate every hour is 2.3%/hr or less.

A description will be given below of the polymerization-reactive compound, the polymerization catalyst, the polymerization initiator, and the composition including the above, which are to be used in the present embodiment.

Examples of polymerization-reactive compounds include a polyiso (thio)cyanate compound having two or more isocyanato groups or isothiocyanato groups, a (thio)epoxide compound having one or more epoxy groups or thioepoxy groups, an oxetanyl compound having one or more oxetanyl groups, a thietanyl compound having one or more thietanyl groups or having an oxetanyl group and a thietanyl group, (meth)acrylate compounds, a (meth)acryloyl compound having one or more methacryloyloxy group, acryloyloxy group, methacryloylthio group, acryloylthio group, methacrylamide group, or acrylamide group, an alkene compound having one or more polymerizable carbon carbon double bond group other than a methacryloyloxy group, an acryloyloxy group, a methacryloylthio group, an acryloylthio group, a methacrylamide group, or an acrylamide group, an alkyne compound having one or more polymerizable carbon-carbon triple bond group, a bifunctional or higher active hydrogen compound, an acid anhydride having one or more acid anhydride group, an allyl carbonate compound, and the like and it is possible to use one kind or two or more kinds of compounds selected from the above.

Examples of polyiso (thio)cyanate compounds include aliphatic polyisocyanate compounds such as tetramethylene diisocyanate, pentamethylene diisocyanate, hexamethylene diisocyanate, heptamethylene diisocyanate, octamethylene diisocyanate, 2,2,4-trimethylhexamethylene diisocyanate, 2,4,4-trimethylhexamethylene diisocyanate, lysine diisocyanato methyl ester, lysine triisocyanate, and xylylene diisocyanate; alicyclic polyisocyanate compounds such as isophorone diisocyanate, bis(isocyanatomethyl)cyclohexane, bis(isocyanatocyclohexyl) methane, dicyclohexyldimethylmethane isocyanate, 2,5-bis(isocyanatomethyl) bicyclo-[2.2.1]-heptane, 2,6-bis(isocyanatomethyl)bicyclo-[2.2.1]-heptane, 3,8-bis(isocyanatomethyl)tricyclodecane, 3,9-bis(isocyanatomethyl)tricyclodecane, 4,8-bis(isocyanatomethyl)tricyclodecane, and 4,9-bis(isocyanatomethyl) tricyclodecane; aromatic polyisocyanate compounds such as tolylene diisocyanate, 4,4'-diphenylmethane diisocyanate, diphenyl sulfide-4,4-diisocyanate, and phenylene diisocyanate; heterocyclic polyisocyanate compounds such as 2,5-diisocyanatothiophene, 2,5-bis(isocyanatomethyl) thiophene, 2,5-diisocyanatotetrahydrothiophene, 2,5-bis (isocyanatomethyl)tetrahydrothiophene, 3,4-bis(isocyanatomethyl)tetrahydrothiophene, 2,5-diisocyanato-1,4-dithiane, 2,5-bis(isocyanatomethyl)-1,4-dithiane, 4,5-diisocyanato-1,3-dithiolane, and 4,5-bis(isocyanatomethyl)-1,3-dithiolane; aliphatic polyisothiocyanate compounds such as hexamethylene diisothiocyanate, lysine diisothiocyanate methyl ester, lysine triisothiocyanate, m-xylylene diisothiocyanate, bis(isothiocyanatomethyl)sulfide, bis(isothiocyanatoethyl)sulfide, and bis(isothiocyanatoethyl)disulfide; alicyclic polyisothiocyanate compounds such as isophorone diisothiocyanate, bis(isothiocyanatomethyl) cyclohexane, bis(isothiocyanatocyclohexyl)methane, cyclohexane diisothiocyanate, methylcyclohexane diisothiocyanate, 2,5-bis(isothiocyanatomethyl)bicyclo-[2.2.1]-heptane, 2,6-bis(isothiocyanatomethyl)bicyclo-[2.2.1]-heptane, 3,8-bis(isothiocyanatomethyl)tricyclodecane, 3,9-bis(isothiocyanatomethyl)tricyclodecane, 4,8-bis (isothiocyanatomethyl)tricyclodecane, and 4,9-bis(isothiocyanatomethyl)tricyclodecane; aromatic polyisothiocyanate compounds such as tolylene diisothiocyanate, 4,4-diphenylmethane diisothiocyanate, and diphenyl disulfide-4,4-diisothiocyanate; sulfur-containing heterocyclic polyisothiocyanate compounds such as 2,5-diisothiocyanatothiophene, 2,5-bis(isothiocyanatomethyl)thiophene, 2,5-isothiocyanatotetrahydrothiophene, 2,5-bis(isothiocyanatomethyl)tetrahydrothiophene, 3,4-bis(isothiocyanatomethyl)tetrahydrothiophene, 2,5-diisocyanato-1,4-dithiane, 2,5-bis(isothiocyanatomethyl)-1,4-dithiane, 4,5-diisothiocyanato-1,3-dithiolane, and 4,5-bis(isothiocyanatomethyl)-1,3-dithiolane, and the like.

Examples of (thio)epoxide compounds include polyepoxy compounds such as bisphenol A diglycidyl ether; chained aliphatic 2,3-epoxypropylthio compounds such as bis(2,3-epoxypropyl) sulfide, bis(2,3-epoxypropyl)disulfide, bis(2,3-epoxypropylthio)methane, 1,2-bis(2,3-epoxypropylthio) ethane, 1,2-bis(2,3-epoxypropylthio)propane, 1,3-bis(2,3-epoxypropylthio)propane, 1,3-bis(2,3-epoxypropylthio)-2-methylpropane, 1,4-bis(2,3-epoxypropylthio)butane, 1,4-bis (2,3-epoxypropylthio)-2-methylbutane, 1,3-bis(2,3-epoxypropylthio)butane, 1,5-bis(2,3-epoxypropylthio) pentane, 1,5-bis(2,3-epoxypropylthio)-2-methylpentane, 1,5-bis(2,3-epoxypropylthio)-3-thiapentane, 1,6-bis(2,3-epoxypropylthio)hexane, 1,6-bis(2,3-epoxypropylthio)-2-methylhexane, 3,8-bis(2,3-epoxypropylthio)-3,6-dithiaoctane, 1,2,3-tris(2,3-epoxypropylthio)propane, 2,2-bis(2,3-epoxypropylthio)-1,3-bis(2,3-epoxypropylthiomethyl) propane, 2,2-bis(2,3-epoxypropylthiomethyl)-1-(2,3-epoxypropylthio)butane, 1,5-bis(2,3-epoxypropylthio)-2-(2, 3-epoxypropylthiomethyl)-3-thiapentane, 1,5-bis(2,3-epoxypropylthio)-2,4-bis(2,3-epoxypropylthiomethyl)-3-thiapentane, 1-(2,3-epoxypropylthio)-2,2-bis(2,3-epoxypropylthiomethyl)-4-thiahexane, 1,5,6-tris (2,3-epoxypropylthio)-4-(2,3-epoxypropylthiomethyl)-3-thiahexane, 1,8-bis(2,3-epoxypropylthio)-4-(2,3-epoxy propylthiomethyl)-3,6-dithiaoctane, 1,8-bis(2,3-epoxypropylthio)-4,5-bis(2,3-epoxypropylthiomethyl)-3,6-dithiaoctane, 1,8-bis(2,3-epoxypropylthio)-4,4-bis(2,3-epoxypropylthiomethyl)-3,6-dithiaoctane, 1,8-bis(2,3-epoxypropylthio)-2,5-bis(2,3-epoxypropylthiomethyl)-3,6-dithiaoctane, 1,8-bis(2, 3-epoxypropylthio)-2,4,5-tris(2,3-epoxy propylthiomethyl)-3,6-dithiaoctane, 1,1,1-tris[[2-(2,3-epoxypropylthio)ethyl] thiomethyl]-2-(2,3-epoxypropylthio)ethane, 1,1,2,2-tetrakis [[2-(2,3-epoxypropylthio)ethyl]thiomethyl]ethane, 1,11-bis (2,3-epoxypropylthio)-4,8-bis(2,3-epoxypropylthiomethyl)-3,6,9-trithiaundecane, 1,11-bis(2,3-epoxypropylthio)-4,7-bis(2,3-epoxypropylthiomethyl)-3,6,9-trithiaundecane, and 1,11-bis(2,3-epoxypropylthio)-5,7-bis(2,3-epoxypropylthiomethyl)-3,6,9-trithiaundecane; cycloaliphatic 2,3-epoxypropylthio compounds such as 1,3-bis(2,3-epoxypropylthio)cyclohexane, 1,4-bis(2,3-epoxypropylthio)cyclohexane, 1,3-bis(2,3-epoxypropylthiomethyl)cyclohexane, 1,4-bis(2,3-epoxypropylthiomethyl)cyclohexane, 2,5-bis(2,3-epoxypropylthiomethyl)-1,4-dithiane, 2,5-bis[[2-(2,3-epoxypropylthio)ethyl]thiomethyl]-1,4-dithiane, and 2,5-bis(2,3-epoxypropylthiomethyl)-2,5-dimethyl-1,4-dithiane;

aromatic 2,3-epoxypropylthio compounds such as 1,2-bis(2,3-epoxypropylthio)benzene, 1,3-bis(2,3-epoxypropylthio)benzene, 1,4-bis(2,3-epoxypropylthio)benzene, 1,2-bis(2,3-epoxypropylthiomethyl)benzene, 1,3-bis(2,3-epoxypropylthiomethyl)benzene, 1,4-bis(2,3-epoxypropylthiomethyl)benzene, bis[4-(2,3-epoxypropylthio)phenyl]methane, 2,2-bis[4-(2,3-epoxypropylthio)phenyl]propane, bis[4-(2,3-epoxypropylthio)phenyl]sulfide, bis[4-(2,3-epoxypropylthio)phenyl]sulfone, and 4,4'-bis(2,3-epoxypropylthio)biphenyl, and the like.

Examples of the thioepoxide compounds (also referred to as an episulfide compound) include epithioethylthio compounds such as bis(1,2-epithioethyl)sulfide, bis(1,2-epithioethyl)disulfide, bis(epithioethylthio)methane, bis(epithioethylthio)benzene, bis[4-(epithioethylthio)phenyl]sulfide, and bis[4-(epithioethylthio)phenyl]methane; chained aliphatic 2,3-epithiopropylthio compounds such as bis(2,3-epithiopropyl)sulfide, bis(2,3-epithiopropyl)disulfide, bis(2,3-epithiopropylthio)methane, 1,2-bis(2,3-epithiopropylthio)ethane, 1,2-bis(2,3-epithiopropylthio)propane, 1,3-bis(2,3-epithiopropylthio)propane, 1,3-bis(2,3-epithiopropylthio)-2-methylpropane, 1,4-bis(2,3-epithiopropylthio)butane, 1,4-bis(2,3-epithiopropylthio)-2-methylbutane, 1,3-bis(2,3-epithiopropylthio)butane, 1,5-bis(2,3-epithiopropylthio)pentane, 1,5-bis(2,3-epithiopropylthio)-2-methylpentane, 1,5-bis(2,3-epithiopropylthio)-3-thiapentane, 1,6-bis(2,3-epithiopropylthio)hexane, 1,6-bis(2,3-epithiopropylthio)-2-methylhexane, 1,8-bis(2,3-epithiopropylthio)-3,6-dithiaoctane, 1,2,3-tris(2,3-epithiopropylthio)propane, 2,2-bis(2,3-epithiopropylthio)-1,3-bis(2,3-epithiopropylthiomethyl) propane, 2,2-bis(2,3-epithiopropylthiomethyl)-1-(2,3-epithiopropylthio)butane, 1,5-bis(2,3-epithiopropylthio)-2-(2,3-epithiopropylthiomethyl)-3-thiapentane, 1,5-bis(2,3-epithiopropylthio)-2,4-bis(2,3-epithiopropylthiomethyl)-3-thiapentane, 1-(2,3-epithiopropylthio)-2,2-bis(2,3-epithiopropylthiomethyl)-4-thiahexane, 1,5,6-tris(2,3-epithiopropylthio)-4-(2,3-epithiopropylthiomethyl-3-thiahexane, 1,8-bis(2,3-epithiopropylthio)-4-(2,3-epithiopropylthiomethyl)-3,6-dithiaoctane, 1,8-bis(2,3-epithiopropylthio)-4,5-bis(2,3-epithiopropylthiomethyl)-3,6-dithiaoctane, 1,8-bis(2,3-epithiopropylthio)-4,4-bis(2,3-epithiopropylthiomethyl)-3,6-dithiaoctane, 1,8-bis(2,3-epithiopropylthio)-2,5-bis(2,3-epithiopropylthiomethyl)-3,6-dithiaoctane, 1,8-bis(2,3-epithiopropylthio)-2,4,5-tris(2,3-epithiopropylthiomethyl)-3,6-dithiaoctane, 1,1,1-tris[[2-(2,3-epithiopropylthio)ethyl]thiomethyl]-2-(2,3-epithiopropylthio)ethane, 1,1,2,2-tetrakis[[2-(2,3-epithiopropylthio)ethyl]thiomethyl]ethane, 1,11-bis(2,3-epithiopropylthio)-4,8-bis(2,3-epithiopropylthiomethyl)-3,6,9-trithiaundecane, 1,11-bis(2,3-epithiopropylthio)-4,7-bis(2,3-epithiopropylthiomethyl)-3,6,9-trithiaundecane, and 1,11-bis(2,3-epithiopropylthio)-5,7-bis(2,3-epithiopropylthiomethyl)-3,6,9-trithiaundecan; cycloaliphatic 2,3-epithiopropylthio compounds such as 1,3-bis(2,3-epithiopropylthio)cyclohexane, 1,4-bis(2,3-epithiopropylthio)cyclohexane, 1,3-bis(2,3-epithiopropylthiomethyl)cyclohexane, 1,4-bis(2,3-epithiopropylthiomethyl)cyclohexane, 2,5-bis(2,3-epithiopropylthiomethyl)-1,4-dithiane, 2,5-bis[2-(2,3-epithiopropylthio)ethyl]thiomethyl]-1,4-dithiane, and 2,5-bis(2,3-epithiopropylthiomethyl)-2,5-dimethyl-1,4-dithiane;

aromatic 2,3-epithiopropylthio compounds such as 1,2-bis(2,3-epithiopropylthio)benzene, 1,3-bis(2,3-epithiopropylthio)benzene, 1,4-bis(2,3-epithiopropylthio)benzene, 1,2-bis(2,3-epithiopropylthiomethyl)benzene, 1,3-bis(2,3-epithiopropylthiomethyl)benzene, 1,4-bis(2,3-epithiopropylthiomethyl)benzene, bis[4-(2,3-epithiopropylthio)phenyl]methane, 2,2-bis[4-(2,3-epithiopropylthio)phenyl]propane, bis[4-(2,3-epithiopropylthio)phenyl]sulfide, bis[4-(2,3-epithiopropylthio)phenyl]sulfone, and 4,4'-bis(2,3-epithiopropylthio)biphenyl; chained aliphatic 2,3-epithiopropyloxy compounds such as bis(2,3-epithiopropyl) ether, bis(2,3-epithiopropyloxy)methane, 1,2-bis(2,3-epithiopropyloxy)ethane, 1,2-bis(2,3-epithiopropyloxy)propane, 1,3-bis(2,3-epithiopropyloxy)propane, 1,3-bis(2,3-epithiopropyloxy)-2-methylpropane, 1,4-bis(2,3-epithiopropyloxy)butane, 1,4-bis(2,3-epithiopropyloxy)-2-methylbutane, 1,3-bis(2,3-epithiopropyloxy)butane, 1,5-bis(2,3-epithiopropyloxy)pentane, 1,5-bis(2,3-epithiopropyloxy)-2-methylpentane, 1,5-bis(2,3-epithiopropyloxy)-3-thiapentane, 1,6-bis(2,3-epithiopropyloxy)hexane, 1,6-bis(2,3-epithiopropyloxy)-2-methylhexane, 1,8-bis(2,3-epithiopropyloxy)-3,6-dithiaoctane, 1,2,3-tris(2,3-epithiopropyloxy)propane, 2,2-bis(2,3-epithiopropyloxy)-1,3-bis(2,3-epithiopropyloxymethyl) propane, 2,2-bis(2,3-epithiopropyloxymethyl)-1-(2,3-epithiopropyloxy)butane, 1,5-bis(2,3-epithiopropyloxy)-2-(2,3-epithiopropyloxymethyl)-3-thiapentane, 1,5-bis(2,3-epithiopropyloxy)-2,4-bis(2,3-epithiopropyloxymethyl-3-thiapentane, 1-(2,3-epithiopropyloxy)-2,2-bis(2,3-epithiopropyloxymethyl)-4-thiahexane, 1,5,6-tris(2,3-epithiopropyloxy)-4-(2,3-epithiopropyloxymethyl)-3-thiahexane, 1,8-bis(2,3-epithiopropyloxy)-4-(2,3-epithiopropyloxymethyl)-3,6-dithiaoctane, 1,8-bis(2,3-epithiopropyloxy)-4,5-bis(2,3-epithiopropyloxymethyl-3,6-dithiaoctane, 1,8-bis(2,3-epithiopropyloxy)-4,4-bis(2,3-epithiopropyloxymethyl-3,6-dithiaoctane, 1,8-bis(2,3-epithiopropyloxy)-2,5-bis(2,3-epithiopropyloxymethyl-3,6-dithiaoctane, 1,8-bis(2,3-epithiopropyloxy)-2,4,5-tris(2,3-epithiopropyloxymethyl)-3,6-dithiaoctane, 1,1,1-tris[[2-(2,3-epithiopropyloxy)ethyl]thiomethyl]-2-(2,3-epi thiopropyloxy)ethane, 1,1,2,2-tetrakis[[2-(2,3-epithiopropyloxy)ethyl]thiomethyl]ethane, 1,11-bis(2,3-epithiopropyloxy)-4,8-bis(2,3-epithiopropyloxymethyl)-3,6,9-trithiaundecane, 1,11-bis(2,3-epithiopropyloxy)-4,7-bis(2,3-epithiopropyloxymethyl)-3,6,9-trithiaundecane, and 1,11-bis(2,3-epithiopropyloxy)-5,7-bis(2,3-epithiopropyloxy methyl)-3,6,9-trithiaundecane; cycloaliphatic 2,3-epithiopropyloxy compounds such as 1,3-bis(2,3-epithiopropyloxy)cyclohexane, 1,4-bis(2,3-epithiopropyloxy)cyclohexane, 1,3-bis(2,3-epithiopropyloxymethyl)cyclohexane, 1,4-bis(2,3-epithiopropyloxymethyl)cyclohexane, 2,5-bis(2,3-epithiopropyloxymethyl)-1,4-dithiane, 2,5-bis[[2-(2,3-epithiopropyloxy)ethyl]thiomethyl]-1,4-dithiane, and 2,5-bis(2,3-epithiopropyloxymethyl)-2,5-dimethyl-1,4-dithiane; and aromatic 2,3-epithiopropyloxy compounds such as 1,2-bis(2,3-epithiopropyloxy)benzene, 1,3-bis(2,3-epithiopropyloxy)benzene, 1,4-bis(2,3-epithiopropyloxy)benzene, 1,2-bis(2,3-epithiopropyloxymethyl)benzene, 1,3-bis(2,3-epithiopropyloxymethyl)benzene, 1,4-bis(2,3- epithiopropyloxymethyl)benzene, bis[4-(2,3-epithiopropyloxy)phenyl]methane, 2,2-bis[4-(2,3-epithiopropyloxy)phenyl]propane, bis[4-(2,3-epithiopropyloxy)phenyl]sulfide, bis[4-(2,3-epithiopropyloxy)phenyl]sulfone, and 4,4'-bis(2,3-epithiopropyloxy)biphenyl, and the like.

It is preferable to use a compound represented by General Formula (3) as the episulfide compound.

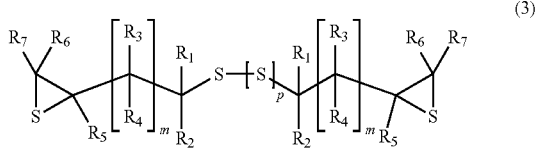

(3)

In General Formula (3), $R_1$ to $R_7$ may be the same or different and represent a hydrogen atom, a linear or branched alkyl group with 1 or more and 10 or less carbon atoms, or a substituted or unsubstituted aryl group with 6 or more and 18 or less carbon atoms. $R_1$ to $R_7$ may be the same or different respectively. Examples of the linear or branched alkyl group with 1 or more and 10 or less carbon atoms include a methyl group, an ethyl group, an n-propyl group, an isopropyl group, an n-butyl group, a sec-butyl group, a tert-butyl group, a pentyl group, a hexyl group, a heptyl group, an octyl group, a nonyl group, a decyl group, and the like.

Examples of the aryl group include aryl groups with 6 or more and 18 or less carbon atoms such as phenyl, tolyl, xylyl, biphenyl, naphthyl, anthryl, and phenanthryl.

Examples of the substituent of the substituted aryl group include an alkyl group with 1 or more and 10 or less carbon atoms, a halogen atom, a hydroxyl group, an alkoxyl group or an alkylthio group with 1 or more and 10 or less carbon atoms, an amino group, or the like.

$R_1$ to $R_7$ may be the same or different and are preferably a hydrogen atom or a linear or branched alkyl group with 1 or more and 10 or less carbon atoms, and all are preferably hydrogen atoms.

m represents an integer of 0 or more and 2 or less, preferably 0 or 1, and more preferably 0. p represents an integer of 0 or more and 4 or less.

Examples of oxetanyl compounds include 3-ethyl-3-hydroxymethyloxetane, 1,4-bis{[(3-ethyl-3-oxetanyl)methoxy]methyl}benzene, 3-ethyl-3-(phenoxymethyl)oxetane, di[1-ethyl-(3-oxetanyl)]methyl ether, 3-ethyl-3-(2-ethylhexyloxymethyl)oxetane, phenol novolac oxetane, and the like.

Examples of thietanyl compounds include 1-{4-(6-mercaptomethylthio)-1,3-dithianylthio}-3-{2-(1,3-dithietanyl)}methyl-7,9-bis(mercaptomethylthio)-2,4,6,10-tetrathiaundecane, 1,5-bis{4-(6-mercaptomethylthio)-1,3-dithianylthio}-3-{2-(1,3-dithietanyl)}methyl-2,4-dithiapentane, 4,6-bis[3-{2-(1,3-dithietanyl)}methyl-5-mercapto-2,4-dithiapentylthio]-1,3-dithiane, 3-{2-(1,3-dithietanyl)}methyl-7,9-bis(mercaptomethylthio)-1,11-dimercapto-2,4,6,10-tetrathiaundecane, 9-{2-(1,3-dithietanyl)}methyl-3,5,13,15-tetrakis(mercaptomethylthio)-1,17-dimercapto-2,6,8,10,12,16-hexathiaheptadecane, 3-{2-(1,3-dithietanyl)}methyl-7,9,13,15-tetrakis(mercaptomethylthio)-1,17-dimercapto-2,4,6,10,12,16-hexathiaheptadecane, 3,7-bis{2-(1,3-dithietanyl)}methyl-1,9-dimercapto-2,4,6,8-tetrathianonane, 4,5-bis[1-{2-(1,3-dithietanyl)}-3-mercapto-2-thiapropylthio]-1,3-dithiolane, 4-[1-{2-(1,3-dithietanyl)}-3-mercapto-2-thiapropylthio]-5-{1,2-bis(mercaptomethylthio)-4-mercapto-3-thiabutylthio}-1,3-dithiolane, 4-{4-(5-mercaptomethylthio-1,3-dithiolanyl)thio}-5-[1-{2-(1,3-di thietanyl)}-3-mercapto-2-thiapropylthio]-1,3-dithiolane, and the like.

It is possible to represent the (meth)acrylate compound by the following formula.

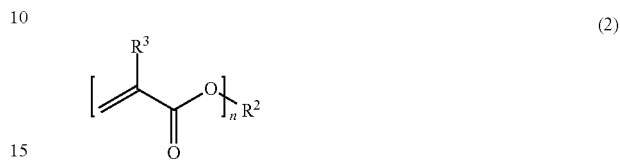

(2)

$R^2$ represents a divalent to tetravalent organic group with 1 to 30 carbon atoms which may include a hetero atom or an aromatic group. $R^3$ represents a hydrogen atom or a methyl group. n represents an integer of 2 to 4.

In addition, examples of the (meth)acrylate compound (B) include compounds represented by General Formula (2-1) and General Formula (2-2).

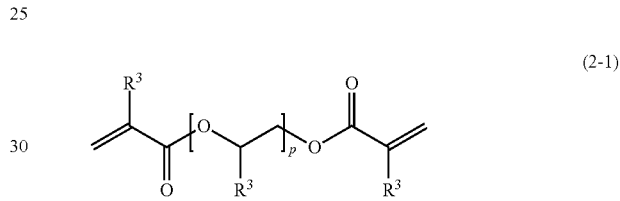

(2-1)

p represents a numerical value of 1 to 100 and $R^3$ represents a hydrogen atom or a methyl group and may not be the same respectively. p is preferably a numerical value of 1 to 50, more preferably a numerical value of 1 to 20, even more preferably a numerical value of 2 to 10, and particularly preferably a numerical value of 2 to 4.

Examples of the (meth)acrylate compound represented by General Formula (2-1) include at least one kind selected from ethylene glycol dimethacrylate, diethylene glycol dimethacrylate, triethylene glycol dimethacrylate, tetraethylene glycol dimethacrylate, ethylene glycol diacrylate, diethylene glycol diacrylate, triethylene glycol diacrylate, tetraethylene glycol diacrylate, propylene glycol dimethacrylate, dipropylene glycol dimethacrylate, tripropylene glycol dimethacrylate, tetrapropylene glycol dimethacrylate, propylene glycol diacrylate, dipropylene glycol diacrylate, tripropylene glycol diacrylate, and tetrapropylene glycol diacrylate.

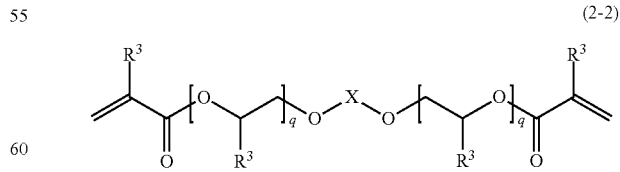

(2-2)

q each represents a numerical value of 1 or more, and the sum of two q represents a numerical value of 2 to 100. $R^3$ represents a hydrogen atom or a methyl group and may not be the same respectively. X represents a substituted or unsubstituted divalent aromatic group or a substituted or unsubstituted divalent aliphatic group, which may include an aromatic group with 1 to 20 carbon atoms.

Examples of the (meth)acrylate compound represented by General Formula (2-2) include at least one kind selected from bisphenol A dimethacrylate, methylene-bis-(4,1-phenylene)-bis-(2-methacrylate), bisphenol A diacrylate, methylene-bis-(4,1-phenylene)-bis-(2-acrylate), 2,2-bis-(4-methacryloyloxyphenyl)propane, 2,2-bis-(4-acryloyloxyphenyl)propane, 2-(4-methacryloyloxyphenyl)-2-(4-methacryloyloxyethoxyphenyl)propane, 2-(4-acryloyloxyphenyl)-2-(4-acryloyloxyethoxyphenyl)propane, 2,2-bis-(4-methacryloyloxyethoxyphenyl)propane, 2,2-bis-(4-acryloyloxyethoxyphenyl)propane, 2-(4-methacryloyloxyethoxyphenyl)-2-(4-(methacryloyloxyethoxy)ethoxyphenyl)propane, 2-(4-acryloyloxyethoxyphenyl)-2-(4-(acryloyloxyethoxy)ethoxyphenyl)propane, 2,2-bis-(4-(methacryloyloxyethoxy)ethoxyphenyl)propane, and 2,2-bis-(4-(acryloyloxyethoxy)ethoxyphenyl)propane.

Examples of (meth)acrylate compounds other than the above include at least one kind selected from the group consisting of butanediol dimethacrylate, hexamethylene dimethacrylate, 2,2-bis(4-methacryloyloxyethoxy-3,5-dibromophenyl)propane, 2,2-bis-(4-methacryloyloxypentaethoxyphenyl)propane, pentaerythritol triacrylate, pentaerythritol tetraacrylate, trimethylolpropane triacrylate, dipentaerythritol hexaacrylate, bisphenol A-diglycidyl ether diacrylate-based, bisphenol A-diglycidyl ether dimethacrylate-based, tetrabromobisphenol A-diglycidyl ether diacrylate-based, and tetrabromobisphenol A-diglycidyl ether dimethacrylate.

Among these exemplified compounds, the (meth)acrylate compound (B) is preferably at least one kind selected from diethylene glycol dimethacrylate, triethylene glycol dimethacrylate, diethylene glycol diacrylate, triethylene glycol diacrylate, dipropylene glycol dimethacrylate, tripropylene glycol dimethacrylate, dipropylene glycol diacrylate, and tripropylene glycol diacrylate, more preferably at least one kind selected from diethylene glycol dimethacrylate, triethylene glycol dimethacrylate, diethylene glycol diacrylate, and triethylene glycol diacrylate, and even more preferably at least one kind selected from diethylene glycol dimethacrylate and triethylene glycol dimethacrylate.

Examples of alkene compounds include polyethylene, polypropylene, polyisobutylene, diethylene glycol bis(allyl carbonate), divinylbenzene, and the like.

Examples of alkyne compounds include hydrocarbon-based alkynes such as 2-butyne, 2-pentyne, 2-hexyne, 3-hexyne, 2-heptyne, 3-heptyne, 2-octyne, 3-octyne, 4-octyne, diisopropylacetylene, 2-nonyne, 3-nonyne, 4-nonyne, 5-nonyne, 2-decyne, 3-decyne, 4-decyne, 5-decyne, di-tert-butylacetylene, diphenylacetylene, dibenzylacetylene, methyl-iso-propylacetylene, methyl-tert-butylacetylene, ethyl-iso-propylacetylene, ethyl-tert-butylacetylene, n-propyl-iso-propyl acetylene, n-propyl-tert-butyl acetylene, phenyl methyl acetylene, phenyl ethyl acetylene, phenyl-n-propylacetylene, phenyl-iso-propylacetylene, phenyl-n-butyl acetylene, and phenyl-tert-butyl acetylene; alkynyl alcohols such as acetylene diol, propynol, butynol, pentynol, hexynol, hexynediol, heptynol, heptynediol, octynol, and octynediol; alkynylamines of which some or all of the OH groups of the alkynyl alcohols are substituted with an NH2 group, and the like.

Examples of bifunctional or higher active hydrogen compounds include poly(thi)ol compounds having two or more hydroxy groups or mercapto groups, polyamine compounds having two or more amino groups or secondary amino groups, polycarboxylic acid compounds having two or more carboxyl groups, and the like. In addition, examples thereof also include a compound having two or more active hydrogen groups selected from a hydroxy group, a mercapto group, an amino group, a secondary amino group, a carboxyl group and the like, in one molecule. Two or more active hydrogen groups may be the same or different.

Among the poly(thi)ol compounds, examples of the polyol compound include aliphatic polyols such as ethylene glycol, diethylene glycol, propylene glycol, dipropylene glycol, tripropylene glycol, butylene glycol, neopentyl glycol, glycerin, trimethylolethane, trimethylolpropane, ditrimethylolpropane, butanetriol, 1,2-methylglucoside, pentaerythritol, dipentaerythritol, tripentaerythritol, sorbitol, erythritol, threitol, ribitol, arabinitol, xylitol, allitol, mannitol, dolcitol, iditol, glycol, inositol, hexanetriol, triglycerose, diglyperol, triethylene glycol, polyethylene glycol, tris(2-hydroxyethyl) isocyanurate, cyclobutanediol, cyclopentanediol, cyclohexanediol, cycloheptanediol, cyclooctanediol, cyclohexanedimethanol, hydroxypropylcyclohexanol, tricyclo[5.2.1.0$^{2,6}$]decane-dimethanol, bicyclo[4.3.0]-nonanediol, dicyclohexanediol, tricyclo[5.3.1.1]dodecanediol, bicyclo[4.3.0]nonanedimethanol, tricyclo[5.3.1.1]dodecane diethanol, hydroxypropyltricyclo[5.3.1.1]dodecanol, spiro[3.4]octanediol, butylcyclohexanediol, 1,1'-bicyclohexylidene diol, cyclohexanetriol, maltitol, and lactose; aromatic polyols such as dihydroxynaphthalene, trihydroxynaphthalene, tetrahydroxynaphthalene, dihydroxybenzene, benzenetriol, biphenyltetraol, pyrogallol, (hydroxynaphthyl)pyrogallol, trihydroxyphenanthrene, bisphenol A, bisphenol F, xylylene glycol, di(2-hydroxyethoxy)benzene, bisphenol A-bis-(2-hydroxyethyl ether), tetrabromobisphenol A, and tetrabromobisphenol A-bis-(2-hydroxyethyl ether); halogenated polyols such as dibromoneopentyl glycol; and polymer polyols such as epoxy resins. In the present embodiment, it is possible to use at least one type selected from the above in a combination.

In addition, as the polyol compound, it is also possible to use other polyol compounds such as condensation reaction products of organic acids such as oxalic acid, glutamic acid, adipic acid, acetic acid, propionic acid, cyclohexane carboxylic acid, β-oxocyclohexane propionic acid, dimer acid, phthalic acid, isophthalic acid, salicylic acid, 3-bromopropionic acid, 2-bromoglycol, dicarboxycyclohexane, pyromellitic acid, butanetetracarboxylic acid, and bromophthalic acid and the above polyols; addition reaction products of the polyols above and alkylene oxides such as ethylene oxide or propylene oxide; addition reaction products of an alkylene polyamine and an alkylene oxide such as ethylene oxide or propylene oxide; furthermore, bis-[4-(hydroxyethoxy)phenyl]sulfide, bis-[4-(2-hydroxypropoxy)phenyl]sulfide, bis-[4-(2,3-dihydroxypropoxy)phenyl]sulfide, bis-[4-(4-hydroxycyclohexyloxy)phenyl]sulfide, bis-[2-methyl-4-(hydroxyethoxy)-6-butylphenyl]sulfide and compounds in which ethylene oxide and/or propylene oxide having an average of 3 molecules or less per hydroxyl group are added to these compounds; polyols containing sulfur atoms such as di-(2-hydroxyethyl)sulfide, 1,2-bis-(2-hydroxyethylmercapto) ethane, bis(2-hydroxyethyl)disulfide, 1,4-dithiane-2,5-diol, bis(2,3-dihydroxypropyl)sulfide, tetrakis(4-hydroxy-2-thiabutyl)methane, bis(4-hydroxyphenyl)sulfone (bisphenol S), tetrabromobisphenol S, tetramethyl bisphenol S, 4,4'-thiobis(6-tert-butyl-3-methylphenol), 1,3-bis(2-hydroxyethylthioethyl)-cyclohexane, and the like. In the present embodiment, it is possible to use at least one type selected from the above in a combination.

Examples of polythiol compounds include aliphatic polythiol compounds such as methanedithiol, 1,2-ethanedithiol, 1,2,3-propanetrithiol, 1,2-cyclohexanedithiol, bis(2-mercaptoethyl)ether, tetrakis(mercaptomethyl)methane, diethylene glycol bis(2-mercaptoacetate), diethylene glycol bis (3-mercaptopropionate), ethylene glycol bis(2-mercaptoacetate), ethylene glycol bis(3-mercaptopropionate), trimethylolpropane tris(2-mercaptoacetate), trimethylolpropane tris(3-mercaptopropionate), trimethylolethane tris(2-mercaptoacetate), trimethylolethane tris(3-mercaptopropionate), pentaerythritol tetrakis(2-mercaptoacetate), pentaerythritol tetrakis(3-mercaptopropionate), bis(mercaptomethyl)sulfide, bis(mercaptomethyl)disulfide, bis(mercaptoethyl)sulfide, bis(mercaptoethyl)disulfide, bis(mercaptopropyl)sulfide, bis(mercaptomethylthio)methane, bis(2-mercaptoethylthio)methane, bis(3-mercaptopropylthio)methane, 1,2-bis(mercaptomethylthio)ethane, 1,2-bis(2-mercaptoethylthio)ethane, 1,2-bis(3-mercaptopropylthio)ethane, 1,2,3-tris(mercaptomethylthio)propane, 1,2,3-tris(2-mercaptoethylthio)propane, 1,2,3-tris(3-mercaptopropylthio)propane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl)sulfide, 2,5-dimercaptomethyl-1,4-dithiane, 2,5-dimercapto-1,4-dithiane, 2,5-dimercaptomethyl-2,5-dimethyl-1,4-dithiane and esters of these compounds with thioglycolic acids and mercaptopropionic acids; hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxymethyl disulfide bis(2-mercaptoacetate), hydroxymethyl disulfide bis(3-mercaptopropinate), hydroxyethyl disulfide bis(2-mercaptoacetate), hydroxyethyl disulfide bis(3-mercaptopropionate), 2-mercaptoethyl ether bis(2-mercaptoacetate), 2-mercaptoethyl ether bis(3-mercaptopropionate), thiodiglycolic acid bis(2-mercaptoethyl ester), thiodipropionic acid bis(2-mercaptoethyl ester), dithiodiglycolic acid bis(2-mercaptoethyl ester), dithiodipropionic acid bis(2-mercaptoethyl ester), 1,1,3,3-tetrakis(mercaptomethylthio)propane, 1,1,2,2-tetrakis(mercaptomethylthio)ethane, 4,6-bis(mercaptomethylthio)-1,3-dithiane, tris(mercaptomethylthio)methane, and tris(mercaptoethylthio)methane; aromatic polythiol compounds such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(mercaptoethyl)benzene, 1,3-bis(mercaptoethyl)benzene, 1,4-bis(mercaptoethyl)benzene, 1,3,5-trimercaptobenzene, 1,3,5-tris(mercaptomethyl)benzene, 1,3,5-tris(mercaptomethyleneoxy)benzene, 1,3,5-tris(mercaptoethyleneoxy)benzene, 2,5-toluenedithiol, 3,4-toluenedithiol, 1,5-naphthalenedithiol, and 2,6-naphthalenedithiol; heterocyclic polythiol compounds such as 2-methylamino-4,6-dithiol-sym-triazine, 3,4-thiophenedithiol, bismuthiol, 4,6-bis(mercaptomethylthio)-1,3-dithiane, and 2-(2,2-bis(mercaptomethylthio)ethyl)-1,3-dithietane, and the like.

Examples of polyamine compounds include primary polyamine compounds such as ethylenediamine, 1,2- or 1,3-diaminopropane, 1,2-, 1,3-, or 1,4-diaminobutane, 1,5-diaminopentane, 1,6-diaminohexane, 1,7-diaminoheptane, 1,8-diaminooctane, 1,10-diaminodecane, 1,2-, 1,3-, or 1,4-diaminocyclohexane, o-, m-, or p-diaminobenzene, 3,4- or 4,4'-diaminobenzophenone, 3,4- or 4,4'-diaminodiphenyl ether, 4,4'-diaminodiphenylmethane, 4,4'-diaminodiphenyl sulfide, 3,3'- or 4,4'-diaminodiphenylsulfone, 2,7-diaminofluorene, 1,5-, 1,8-, or 2,3-diaminonaphthalene, 2,3-, 2,6-, or 3,4-diaminopyridine, 2,4- or 2,6-diaminotoluene, m- or p-xylylenediamine, isophoronediamine, diaminomethylbicycloheptane, 1,3- or 1,4-diaminomethylcyclohexane, 2- or 4-aminopiperidine, 2- or 4-aminomethylpiperidine, 2- or 4-aminoethylpiperidine, N-aminoethylmorpholine, and N-aminopropylmorpholine; monofunctional secondary amine compounds such as diethylamine, dipropylamine, di-n-butylamine, di-sec-butylamine, diisobutylamine, di-n-pentylamine, di-3-pentylamine, dihexylamine, dioctylamine, di(2-ethylhexyl)amine, methyl hexyl amine, diallylamine, N-methylallylamine, piperidine, pyrrolidine, diphenylamine, N-methylamine, N-ethylamine, dibenzylamine, N-methylbenzylamine, N-ethylbenzylamine, dicyclohexylamine, N-methylaniline, N-ethylaniline, dinaphthylamine, 1-methylpiperazine, and morpholine; secondary polyamine compounds such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diamino hexane, N,N'-dimethyl-1,7-diaminoheptane, N,N'-diethylethylenediamine, N,N'-diethyl-1,2-diaminopropane, N,N'-diethyl-1,3-diamino propane, N,N'-diethyl-1,2-diaminobutane, N,N'-diethyl-1,3-diaminobutane, N,N'-diethyl-1,4-diaminobutane, N,N'-diethyl-1,5-diaminopentane, N,N'-diethyl-1,6-diaminohexane, N,N'-diethyl-1,7-diaminoheptane, piperazine, 2-methylpiperazine, 2,5-dimethylpiperazine, 2,6-dimethylpiperazine, homopiperazine, 1,1-di-(4-piperidyl)methane, 1,2-di-(4-piperidyl)ethane, 1,3-di-(4-piperidyl)propane, 1,4-di-(4-piperidyl)butane, and tetramethylguanidine; and the like.

Examples of polycarboxylic acid compounds include succinic acid, adipic acid, sebacic acid, azelaic acid, dodecanedioic acid, terephthalic acid, isophthalic acid, orthophthalic acid, phthalic anhydride, tetrahydrophthalic acid, hexahydrophthalic acid, naphthalenedicarboxylic acid, biphenyl dicarboxylic acid, dimer acid, trimellitic acid, pyromellitic acid, ε-caprolactone, and the like.

Examples of the compound having two or more different active hydrogen groups include a hydroxythiol compound having one or more mercapto groups and one or more hydroxyl groups, and the like.

Examples of the hydroxythiol compound include 2-mercaptoethanol, 3-mercapto-1,2-propanediol, glycerin di(mercaptoacetate), 1-hydroxy-4-mercaptocyclohexane, 2,4-dimercaptophenol, 2-mercaptohydroquinone, 4-mercaptophenol, 3,4-dimercapto-2-propanol, 1,3-dimercapto-2-propanol, 2,3-dimercapto-1-propanol, 1,2-dimercapto-1,3-butanediol, pentaerythritol tris(3-mercaptopropionate), pentaerythritol mono(3-mercaptopropionate), pentaerythritol bis(3-mercaptopropionate), pentaerythritol tris(thioglycolate), pentaerythritol pentakis(3-mercaptopropionate), hydroxymethyl-tris(mercaptoethylthiomethyl)methane, 1-hydroxyethylthio-3-mercaptoethylthiobenzene, 4-hydroxy-4'-mercaptodiphenyl sulfone, 2-(2-mercaptoethylthio)ethanol, dihydroxyethylsulfide mono(3-mercaptopropionate), dimercaptoethane mono(salicylate), hydroxyethylthiomethyl-tris(mercaptoethylthio)methane, and the like.

Examples of acid anhydrides include succinic anhydride, phthalic anhydride, maleic anhydride, tetrabromophthalic anhydride, tetrahydrophthalic anhydride, trimellitic anhydride, dodecylsuccinic anhydride, and the like.

It is possible to represent the allyl carbonate compound by the following formula.

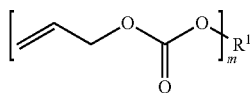

R[1] represents a chained or branched divalent to 20-valent group derived from an aliphatic polyol with 3 to 35 carbon atoms which may include a hetero atom, or a divalent to 20-valent group derived from a cycloaliphatic polyol with 5 to 40 carbon atoms which may include a hetero atom. m represents an integer of 2 to 10. Furthermore, R[1] does not include an allyloxycarbonyl group.

It is possible for the allyl carbonate compound to include an oligomer thereof. The oligomer is, for example, poly(allyl carbonate) produced by a transesterification reaction between a diallyl carbonate and a polyol and in which two or more molecules of a polyol are linked via a carbonate bond. The allyl carbonate compound is a poly(allyl carbonate) of a chained or branched chain aliphatic polyol having 3 to 35 carbon atoms. A poly(allyl carbonate) of a cycloaliphatic polyol having 5 to 40 carbon atoms in the molecule is also suitable for this purpose. These polyols usually able to have 2 to 6 hydroxyl groups in the molecule, and preferably to have 2 to 4. It is also possible to use a mixed poly(allyl carbonate), that is, a poly(allyl carbonate) derived from two or more kinds of polyols and obtainable by mixing poly(allyl carbonate) s of a single polyol, or a poly(allyl carbonate) directly obtainable by a chemical reaction starting from a polyol mixture and a diallyl carbonate. Finally, it is possible for all these poly(allyl carbonates) to take the form of monomers or mixtures of monomers and oligomers.

Specific examples of the polyol forming R[1] in General Formula (1) include diethylene glycol, dipropylene glycol, triethylene glycol, tetraethylene glycol, 1,3-propanediol, 1,4-butanediol, 1,5-pentanediol, 1,6-hexanediol, neopentyl glycol, 3-methyl-1,5-pentanediol, 2-methyl-2-ethyl-1,3-propanediol, 2,2-diethyl-1,3-propanediol, 2,2,4-trimethyl-1,3-pentanediol, 1,4-dimethylolcyclohexane, 4,8-bis(hydroxymethyl)-[5.2.1.0$^{2,6}$]tricyclodecane, glycerol, trimethylolpropane, tris(hydroxyethyl)isocyanurate, pentaerythritol, diglycerol, ditrimethylolpropane, dipentaerythritol, and the like.

Accordingly, examples of allyl carbonate compounds include at least one kind selected from: bis(allyl carbonate) compound of at least one kind of diol selected from diethylene glycol, dipropylene glycol, triethylene glycol, tetraethylene glycol, 1,3-propanediol, 1,4-butanediol, 1,5-pentanediol, 1,6-hexanediol, neopentyl glycol, 3-methyl-1,5-pentanediol, 2-methyl-2-ethyl-1,3-propanediol, 2,2-diethyl-1,3-propanediol, 2,2,4-trimethyl-1,3-pentanediol, 1,4-dimethylolcyclohexane, and 4,8-bis(hydroxymethyl)-[5.2.1.0$^{2,6}$]tricyclodecane; tris(allyl carbonate) compound of at least one kind of triol selected from glycerol, trimethylol propane, and tris(hydroxyethyl)isocyanurate; tetra(allyl carbonate) compound of at least one kind of tetraol selected from pentaerythritol, diglycerol, and ditrimethylolpropane; a hexa (allyl carbonate) compound of dipentaerythritol; and a mixed poly(allyl carbonate) compound of at least two kinds of compounds selected from the diol, the triol, the tetraol and the dipentaerythritol.

Furthermore, "the bis(allyl carbonate) of a mixture of at least two types of diols" is, for example, obtained as a mixture of the following monomer components and oligomer components in a case where the diol is diethylene glycol and neopentyl glycol.

Monomer Components
(1) Diethylene glycol bis(allyl carbonate)
(2) Neopentyl glycol bis(allyl carbonate)

Oligomer Components
(3) Oligomer including only hydrocarbon (and ether) derived from diethylene glycol
(4) Oligomer including only hydrocarbon derived from neopentyl glycol
(5) Complex oligomer including both hydrocarbon (and ether) derived from diethylene glycol and hydrocarbon derived from neopentyl glycol The following are preferable examples of allyl carbonate polymerizable compounds suitable for the purpose of the present invention.

(i) Mixture of bis(allyl carbonate) compound of diethylene glycol and oligomer thereof It is possible to define the diethylene glycol bis(allyl carbonate) by Formula (1-1).

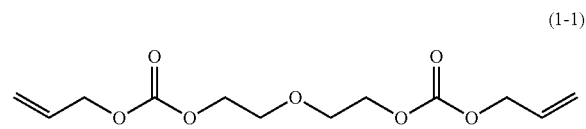 [SMILES: C=CCOC(=O)OCCOCCOC(=O)OCC=C]

In addition, it is possible to define the oligomer of diethylene glycol bis(allyl carbonate) by Formula (1-2).

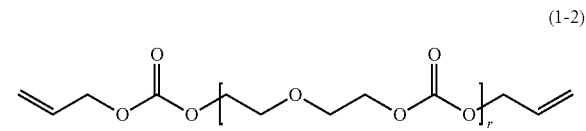

In the formula, r is 2 or more.

It is possible to manufacture compound (1-1) by reacting diethylene glycol bis(chloroformate) with allyl alcohol as described, for example, in "Encyclopedia of Chemical Technology", Kirk-Othmer, version III, Volume 2, pages 111-112. It is possible to easily manufacture a mixture of diethylene glycol bis(allyl carbonate) (Formula (1-1)) and an oligomer thereof (Formula (1-2)), for example, by transesterification of diallyl carbonate and diethylene glycol by operating in the presence of a basic catalyst as described in the specification of European Patent No. 35,304. These mixtures usually include up to approximately 80% by weight of oligomers.

(ii) Mixture of bis(allyl carbonate) compound of a mixture of diethylene glycol and neopentyl glycol and oligomer thereof This bis(allyl carbonate) compound is the same as the bis(allyl carbonate) in (i), except that the diethylene glycol is substituted with a mixture of diethylene glycol and neopentyl glycol.

(iii) Mixture of Poly(allyl carbonate) compound of a mixture of diethylene glycol and tris(hydroxyethyl) isocyanurate and oligomer thereof It is possible to obtain the poly(allyl carbonate) compound, for example, by transesterification of a diallyl carbonate of a mixture of diethylene glycol and tris(hydroxyethyl)isocyanurate as described in U.S. Pat. No. 4,812,545.

(iv) Mixture of poly(allyl carbonate) compound of a mixture of diethylene glycol and trimethylolpropane and oligomer thereof This poly(allyl carbonate) compound is the same as the poly(allyl carbonate) in (iii), except that the tris(hydroxyethyl)isocyanurate is substituted with trimethylol propane.

(v) Mixture of poly(allyl carbonate) compound of a mixture of diethylene glycol and pentaerythritol and oligomer thereof This poly(allyl carbonate) compound is the same as the poly(allyl carbonate) compound in (iii) except that the tris(hydroxyethyl)isocyanurate is substituted with pentaerythritol.

(vi) Mixture of poly(allyl carbonate) compound of a mixture of diethylene glycol, neopentyl glycol, and pentaerythritol and oligomer thereof This poly(allyl carbonate) compound is the same as the poly(allyl carbonate) compound in (v) except that the diethylene glycol is substituted with two kinds of diols of diethylene glycol and neopentyl glycol.

(vii) A poly(allyl carbonate) mixture including a mixture of a poly(allyl carbonate) compound of a mixture of diethylene glycol, neopentyl glycol, and pentaerythritol and an oligomer thereof, and a mixture of a bis(allyl carbonate) compound of diethylene glycol and an oligomer thereof A more detailed description will be given of the cured resin forming the optical material in the present embodiment. The cured resin is obtained by heating and polymerizing a composition including a polymerization-reactive compound and a polymerization catalyst and/or a polymerization initiator, and is preferably a cured resin obtained from a liquid composition for which a casting operation is easy and, among such cured resins, the following cured resins according to (a1) to (a29) are preferable.

(a1) A poly(thio)urethane resin obtained by polymerizing a polyiso(thio)cyanate compound and a poly(thi)ol compound In the present application, poly(thio)urethane resin means a polyurethane resin, a polythiourethane resin, or a polydithiourethane resin.

(a2) A poly(thio)urea resin obtained by polymerizing a polyisocyanate compound or a polyisothiocyanate compound and a polyamine compound In the present application, poly(thio)urea resin means a polyurea resin and a polythiourea resin.

(a3) A polythiourethane-polyurea resin or polydithiourethane-polyurea resin obtained by polymerizing a polyisocyanate compound or polyisothiocyanate compound with a polyamine compound and a polythiol compound (a4) A polythiourethane-polyurethane resin or polydithiourethane-polyurethane resin obtained by polymerizing a polyisocyanate compound or polyisothiocyanate compound with a polyol compound and a polythiol compound (a5) A poly(thio)epoxide resin obtained by polymerizing a (thio)epoxide compound (a6) A poly(thio)epoxide-poly(thi)ol resin obtained by polymerizing a (thio)epoxide compound and a poly(thi)ol compound (a7) A poly(thio)epoxide-polyamine resin obtained by polymerizing a (thio)epoxide compound and a polyamine compound (a8) A poly(thio)epoxide-acid anhydride resin obtained by polymerizing a (thio)epoxide compound and an acid anhydride (a9) A poly(meth)acryloyl resin obtained by polymerizing a (meth)acryloyl compound (a10) A poly(meth)acryloyl-poly(thi)ol resin obtained by polymerizing a (meth)acryloyl compound and a poly(thi)ol compound (a11) A poly(meth)acryloyl-polyalkene resin obtained by polymerizing a (meth)acryloyl compound and an alkene compound (a12) A poly(meth)acryloyl-polyalkyne resin obtained by polymerizing a (meth)acryloyl compound and an alkyne compound (a13) A poly(meth)acryloyl-polyamine resin obtained by polymerizing a (meth)acryloyl compound and a polyamine compound (a14) A poly(meth)acrylate resin obtained by polymerizing a (meth)acrylate compound (a15) A polyallyl carbonate resin obtained by polymerizing an allyl carbonate compound (a16) A poly(meth)acrylate-allyl carbonate resin obtained by polymerizing a (meth)acrylate compound and allyl carbonate compound (a17) A polyalkene resin obtained by polymerizing an alkene compound (a18) A polyalkene-poly(thi)ol resin obtained by polymerizing an alkene compound and a poly(thi)ol compound (a19) A polyalkene-polyamine resin obtained by polymerizing an alkene compound and a polyamine compound (a20) A polyalkyne resin obtained by polymerizing an alkyne compound (a21) A polyalkyne-poly(thi)ol resin obtained by polymerizing an alkyne compound and a poly(thi)ol compound (a22) A polyalkyne-polyamine resin obtained by polymerizing an alkyne compound and a polyamine compound (a23) A polyalkyne-polyalkene resin obtained by polymerizing an alkyne compound and an alkene compound (a24) A polyoxetanyl resin obtained by polymerizing an oxetanyl compound (a25) A polyoxetanyl-poly(thi)ol resin obtained by polymerizing an oxetanyl compound and a poly(thi)ol compound (a26) A polyoxetanyl-polyamine resin obtained by polymerizing an oxetanyl compound and a polyamine compound (a27) A polyoxetanyl-acid anhydride resin obtained by polymerizing an oxetanyl compound and an acid anhydride (a28) A polythietanyl-poly(thi)ol resin obtained by polymerizing a thietanyl compound and a poly(thi)ol compound (a29) A polythietanyl-polyamine resin obtained by polymerizing a thietanyl compound and a polyamine compound (a30) A polythietanyl-acid anhydride resin obtained by polymerizing a thietanyl compound and an acid anhydride (a31) A mixed resin obtained by copolymerizing two or more types selected from (a1) to (a30)

Among the cured resins described above in (a1) to (a31), examples of more preferable cured resins include the resins described in (a1) to (a4), (a6), and (a14) to (a16), and mixed resins thereof (mixtures of a copolymer and a resin).

[Other Components Such as Additives]

The polymerizable composition used in the present embodiment may include components other than the polymerization-reactive compound and the modifiers described above such as polyether-modified compound, the ester compound, or the ether compound.

Examples thereof include a monofunctional iso(thio)cyanate compound, a monofunctional (thio)epoxy compound, a monofunctional oxetanyl compound, a monofunctional thietanyl compound, a monofunctional (meth)acryloyl compound having one functional group freely selected from a methacryloyloxy group, an acryloyloxy group, a methacryloylthio group, an acryloylthio group, a methacrylamide group, or an acrylamide group, a monofunctional alkene compound having one polymerizable carbon-carbon double bond other than a methacryloyloxy group, an acryloyloxy group, a methacryloylthio group, an acryloylthio group, a methacrylamide group, or an acrylamide group, a monofunctional alcohol compound other than alcohol used as a solvent, a monofunctional thiol compound, a monofunctional amine compound having one functional group freely selected from an amino group or a secondary amino group, a monofunctional carboxylic acid compound having one carboxyl group, a solvent, moisture, and the like.

In the process of cast polymerizing the composition of the present embodiment to manufacture a molded article, a polymerization catalyst or a thermal polymerization initiator is added in a case of curing by heat, and a photopolymerization initiator is added in a case of curing by radiation other than infrared rays (heat), such as ultraviolet rays.

Examples of polymerization catalysts include a Lewis acid, an amine compound, a tertiary amine compound and an inorganic acid salt or an organic acid salt thereof, a metal compound, aquaternary ammonium salt, an organic sulfonic acid, and the like.

The usage amount of the polymerization catalyst with respect to the polymerizable composition is preferably in the range of 5 ppm to 15% by weight, more preferably in the range of 10 ppm to 10% by weight, and even more preferably in the range of 50 ppm to 3% by weight.

Examples of metal compounds to be used as polymerization catalysts include dimethyltin chloride, dibutyltin chloride, dibutyltin laurate, and the like.

Examples of the thermal polymerization initiator to be used include ketone peroxide compounds such as methyl isobutyl ketone peroxide and cyclohexanone peroxide; diacyl peroxide compounds such as isobutyryl peroxide, o-chlorobenzoyl peroxide and benzoyl peroxide; dialkyl peroxide compounds such as tris(t-butylperoxy)triazine and t-nutylcumyl peroxide; peroxyketal compounds such as 1,1-di(t-hexylperoxy)cyclohexane, 2,2-bis(4,4-di-t-butylperoxycyclohexyl)propane, 2,2-di(t-butylperoxy)butane and 1,1-di(t-amylperoxy)cyclohexane; alkyl peroxyester compounds such as α-cumyl peroxyneodecanoate, t-butyl peroxypivalate, 2,4,4-trimethylpentyl peroxy-2-ethylhexanoate, t-butyl peroxy-2-ethyl hexanoate, t-butyl peroxy-3,5,5-trimethylhexanoate, and t-amyl peroxyneodecanoate; peroxycarbonate compounds such as di-3-methoxybutylperoxydicarbonate, bis(4-t-butylcyclohexyl)peroxydicarbonate, t-butylperoxyisopropyl carbonate, and diethylene glycol bis(t-butylperoxycarbonate), and the like.

Examples of the photopolymerization initiator to be used include a photoradical polymerization initiator, a photocationic polymerization initiator, a photoanionic polymerization initiator, and the like, and, among these photopolymerization initiators, a photoradical polymerization initiator is preferable.

Examples of the photoradical polymerization initiators include Irgacure 127 (manufactured by BASF), Irgacure 651 (manufactured by BASF), Irgacure 184 (manufactured by BASF), Darocur 1173 (manufactured by BASF), benzophenone, 4-phenyl benzophenone, Irgacure 500 (manufactured by BASF), Irgacure 2959 (manufactured by BASF), Irgacure 907 (manufactured by BASF), Irgacure 369 (manufactured by BASF), Irgacure 1300 (manufactured by BASF), Irgacure 819 (manufactured by BASF), Irgacure 1800 (manufactured by BASF), Darocur TPO (manufactured by BASF), Darocur 4265 (manufactured by BASF), Irgacure OXE 01 (manufactured by BASF), Irgacure OXE 02 (manufactured by BASF), Esacure KT 55 (manufactured by Lamberti), Esacure ONE (manufactured by Lamberti), Esacure KIP 150 (manufactured by Lamberti), Esacure KIP 100 F (manufactured by Lamberti), Esacure KT 37 (manufactured by Lamberti), Esacure KTO 46 (manufactured by Lamberti), Esacure 1001M (manufactured by Lamberti), Esacure KIP/EM (manufactured by Lamberti), Esacure DP250 (manufactured by Lamberti), Esacure KB 1 (manufactured by Lamberti), 2,4-diethylthioxanthone, and the like.

Among these photoradical polymerization initiators, Irgacure 127 (manufactured by BASF), Irgacure 184 (manufactured by BASF), Darocur 1173 (manufactured by BASF), Irgacure 500 (manufactured by BASF), Irgacure 819 (manufactured by BASF), Darocur TPO (manufactured by BASF), Esacure ONE (manufactured by Lamberti), Esacure KIP 100 F (manufactured by Lamberti), Esacure KT 37 (manufactured by Lamberti), Esacure KTO 46 (manufactured by Lamberti), and the like are preferable.

Examples of photocationic polymerization initiators include Irgacure 250 (manufactured by BASF), Irgacure 784 (manufactured by BASF), Esacure 1064 (manufactured by Lamberti), Cyraure UVI 6990 (manufactured by Union Carbide Japan Ltd.), Adeka Optomer SP-172 (manufactured by ADEKA), Adeka Optomer SP-170 (manufactured by ADEKA), Adeka Optomer SP-152 (manufactured by ADEKA), and Adeka Optomer SP-150 (manufactured by ADEKA), and the like.

In a case where the photopolymerization initiator described above is used, a photopolymerization accelerator may be used in combination therewith. Examples of photopolymerization accelerators include 2,2-bis(2-chlorophenyl)-4,5'-tetraphenyl-2'H-<1,2'>biimidazoleyl, tris(4-dimethylaminophenyl)methane, 4,4'-bis(dimethylamino)benzophenone, 2-ethylanthraquinone, camphorquinone, and the like.

The usage amount of the photopolymerization initiator and the thermal polymerization initiator in the polymerizable composition is preferably in the range of 0.1 to 20% by weight, more preferably in the range of 0.5 to 10% by weight, and even more preferably in the range of 1 to 5% by weight.

The composition in the present embodiment preferably has the following configuration from the viewpoint of the effects of the present invention.

Composition (1): a composition including a polyisocyanate compound and an active hydrogen compound as polymerization-reactive compounds, and the polymerization catalyst.

Composition (2): a composition including at least one kind of compounds selected from an allyl carbonate compound, a (meth)acrylate compound, or an episulfide compound as a polymerization-reactive compound, and the polymerization initiator or the polymerization catalyst.

In the composition (1), the polyisocyanate compound preferably includes at least one kind selected from aliphatic polyisocyanates, aromatic polyisocyanates, heterocyclic polyisocyanates, and alicyclic polyisocyanates, and the active hydrogen compound preferably includes at least one kind selected from the group consisting of polythiol compounds having two or more mercapto groups, hydroxythiol compounds having one or more mercapto groups and one or more hydroxyl groups, polyol compounds having two or more hydroxyl groups, and amine compounds.

In the composition (2), the allyl carbonate compound is preferably represented by General Formula (1), the (meth) acrylate compound is preferably represented by General Formula (2), and the episulfide compound is preferably represented by General Formula (3).

In addition, in the process of cast polymerizing the composition of the present embodiment to manufacture a molded article, an internal release agent may be added as necessary.

As the internal release agent, it is possible to use an acidic phosphate ester. Examples of acidic phosphate esters include phosphoric acid monoesters and phosphoric acid diesters, which may be used alone or in a combination of two or more types.

It is possible to represent the acidic phosphate ester used as an internal release agent by General Formula (a).

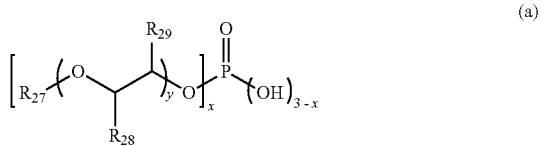

(a)

In General Formula (a), x represents an integer of 1 or 2, y represents an integer of 0 to 18, $R_{27}$ represents an alkyl group having 1 to 20 carbon atoms, and $R_{29}$ and $R_{29}$ each independently represents a hydrogen atom, a methyl group, or an ethyl group. The number of carbon atoms in [ ] x is preferably 4 to 20. Plural present $R_{27}$, plural present $R_{28}$, or plural present $R_{29}$ may be the same or different from each other.

Examples of $R_{27}$ in General Formula (a) include organic residues derived from linear aliphatic compounds such as methane, ethane, propane, butane, pentane, hexane, heptane, octane, nonane, decane, undecane, dodecane, tetradecane, and hexadecane; organic residues derived from branched chain aliphatic compounds such as 2-methylpropane, 2-methylbutane, 2-methylpentane, 3-methylpentane, 3-ethylpentane, 2-methylhexane, 3-methylhexane, 3-ethylhexane, 2-methylheptane, 3-methylheptane, 4-methylheptane, 3-ethylheptane, 4-ethylheptane, 4-propylheptane, 2-methyloctane, 3-methyloctane, 4-methyloctane, 3-ethyloctane, 4-ethyloctane, and 4-propyloctane; organic residues derived from alicyclic compounds such as cyclopentane, cyclohexane, 1,2-dimethylcyclohexane, 1,3-dimethylcyclohexane and 1,4-dimethylcyclohexane, and the like and it is possible to use at least one type selected from the above. Note that the present invention is not limited only to these exemplified compounds. It is possible to use at least one type or a mixture of two or more types of acidic phosphate esters.

In General Formula (a) described above, y is preferably 0 or 1.

In a case where y is 0, $R_{27}$ is preferably a linear or branched alkyl group having 4 to 12 carbon atoms, and more preferably a linear alkyl group having 4 to 12 carbon atoms.

In a case where y is 1, $R_{27}$ is preferably a linear or branched alkyl group having 1 to 20 carbon atoms and is more preferably a linear or branched alkyl group having 3 to 12 carbon atoms.

It is possible to use the acidic phosphate ester as one type or a mixture of two or more types selected from the above.

Examples of acidic phosphate esters include ZelecUN (manufactured by STEPAN), internal release agents for MR (manufactured by Mitsui Chemicals, Inc.), the JP series manufactured by Johoku Chemical Co., Ltd., the phosphanol series manufactured by Toho Chemical Industry Co., Ltd. and the AP and DP series manufactured by Daihachi Chemical Industry Co., Ltd., and ZelecUN (manufactured by Stepan), and internal release agents for MR (manufactured by Mitsui Chemicals, Inc.) are more preferable.

In order to prevent the molded article formed of the cured resin in the present embodiment from deteriorating even when exposed to the outside for a long period of time, it is desirable to further add an ultraviolet absorber and a hindered amine light stabilizer to the composition in the present embodiment to impart weatherability thereto.

The ultraviolet absorber described above is not particularly limited, and, for example, it is possible to use various ultraviolet absorbers such as a benzotriazole-based ultraviolet absorber, a triazine-based ultraviolet absorber, a benzophenone-based ultraviolet absorber, a benzoate-based ultraviolet absorber, a propanedioic acid ester-based ultraviolet absorber, or an oxanilide-based ultraviolet absorber.

Specifically, examples of ultraviolet absorbers include benzotriazole-based ultraviolet absorbers such as 2-(2H-benzotriazol-2-yl)-4-methyl-6-(3,4,5,6-tetrahydrophthalibidylmethyl)phenol, 2-(2H-benzotriazole-2-yl)-p-cresol, 2-(2H-benzotriazole-2-yl)-4-tert-butylphenol, 2-(2H-benzotriazole-2-yl)-4,6-di-tert-butylphenol, 2-(2H-benzotriazole-2-yl)-4,6-bis(1-methyl-1-phenylethyl)phenol, 2-(2H-benzotriazole-2-yl)-4-(1,1,3,3-tetramethylbutyl)-6-(1-meth yl-1-phenyl ethyl)phenol, 2-(2H-benzotriazole-2-yl)-4-(3-on-4-oxa-dodecyl)-6-tert-butyl-phenol, 2-{5-chloro(2H)-benzotriazole-2-yl}-4-(3-on-4-oxa-dodecyl)-6-tert-butyl-phenol, 2-{5-chloro(2H)-benzotriazole-2-yl}-4-methyl-6-tert-butyl-phenol, 2-(2H-benzotriazole-2-yl)-4,6-di-tert-pentylphenol, 2-{5-chloro (2H)-benzotriazole-2-yl}-4,6-di-tert-butylphenol, 2-(2H-benzotriazole-2-yl)-4-tert-octylphenol, 2-(2H-benzotriazole-2-yl)-4-methyl-6-n-dodecyl phenol, 3-[3-tert-butyl-5-(5-chloro-2H-benzotriazole-2-yl)-4-hydroxyphenyl]octyl propionic acid, 3-[3-tert-butyl-5-(5-chloro-2H-benzotriazole-2-yl)-4-hydroxyphenyl]propionic acid 2-ethylhexyl, reaction product of methyl-3-{3-(2H-benzotriazole-2-yl)-5-tert-butyl-4-hydroxyphenyl}propionate/polyethylene glycol 300, trade name Viosorb 583 (manufactured by Kyodo Chemical Co., Ltd.), trade name Tinuvin 326 (manufactured by BASF), trade name Tinuvin 384-2 (manufactured by BASF), trade name Tinuvin PS (manufactured by BASF), trade name Seesorb 706 (manufactured by Shipro Kasei Kaisha, Ltd.), and trade name Eversorb 109 (manufactured by Everlight); triazine-based ultraviolet absorbers such as 2-(4-phenoxy-2-hydroxy-phenyl)-4,6-diphenyl-1,3,5-triazine, 2-(2-hydroxy-4-oxa-hexadecyloxy)-4,6-di(2,4-dimethyl-phenyl)-1, 3,5-triazine, 2-(2-hydroxy-4-oxa-heputadecyloxy)-4,6-di(2, 4-dimethyl-phenyl)-1,3,5-triazine, 2-(2-hydroxy-4-isooctyloxy-phenyl)-4,6-di(2,4-dimethyl-phenyl)-1,3,5-triazine, trade name Tinuvin 400 (manufactured by BASF), trade name Tinuvin 405 (manufactured by BASF), trade name Tinuvin 460 (manufactured by BASF), and trade name Tinuvin 479 (manufactured by BASF); benzophenone-based ultraviolet absorbers such as 2-hydroxy-4-n-methoxybenzophenone and 2-hydroxy-4-n-octoxybenzophenone; benzoate-based ultraviolet absorbers such as 2,4-di-tert-butyl phenyl-3,5-di-tert-butyl-4-hydroxybenzoate; propanedioccitan acid ester-based ultraviolet absorbers such as propanedioccitan acid-{(4-methoxyphenyl)-methylene}-dimethyl ester, trade name Hostavin PR-25 (manufactured by Clariant Japan Co., Ltd.), and trade name Hostavin B-CAP (manufactured by Clariant Japan Co., Ltd.); oxanilide-based ultraviolet absorbers such as 2-ethyl-2'-ethoxy-oxanilide and trade name Sanduvor VSU (manufactured by Clariant Japan Co., Ltd.); and the like. Among these ultraviolet absorbers, benzotriazole-based and triazine-based ultraviolet absorbers tend to be preferable.

Furthermore, a light-control dye or a light-control pigment may be added for the purpose of imparting light-control properties. It is possible to use one type or two or more types as representative light-control dyes or light-control pigments, for example, from spiropyran-based compounds, spirooxazine-based compounds, fulgide-based compounds, naphthopyran-based compounds, and bisimidazole compounds, according to the desired coloration.

To the composition of the present embodiment, various additives may be further added as necessary, such as a polymerization accelerator, a catalyst, an infrared absorber, a radical scavenger, an antioxidant, a polymerization inhibitor, a non-light-control pigment and dye, a binder, a dispersant, an antifoaming agent, and nanometer-sized organic or inorganic particles.

A cured resin obtained by heating and polymerizing the composition of the present embodiment and a molded article formed of the resin are manufactured by adding a polymerization-reactive compound and, as necessary, the various additives and the like described above. In addition, a polymerization-reactive compound, an additive, and the like not described in the present application may be added to the composition in the present embodiment as long as the effects of the present invention are not impaired.

A description will be given below of the method for setting polymerization condition and the apparatus for setting polymerization condition 10 according to the present embodiment.

Figure 2:
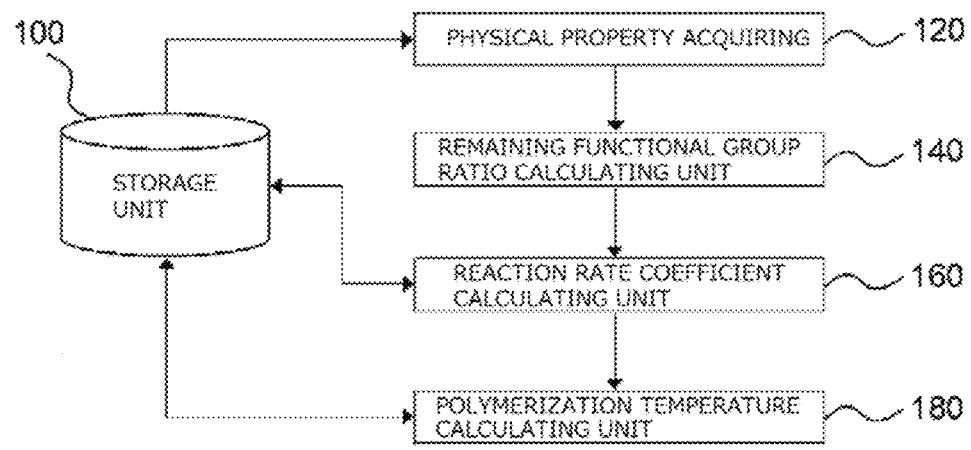
FIG. 2 is a block diagram illustrating a configuration of a apparatus for setting polymerization condition according to the present embodiment.

FIG. 2 is a block diagram illustrating a configuration of the apparatus for setting polymerization condition 10 according to the present embodiment. The setting device 10 according to the present embodiment is a setting device which calculates polymerization conditions in the composition described above.

The setting device 10 is provided with the physical property acquiring unit 120, the remaining functional group ratio calculating unit 140, the reaction rate coefficient calculating unit 160, and the polymerization temperature calculating unit 180.

The apparatus for setting polymerization condition 10 is further provided with the storage unit 100. The storage unit is a computer-readable medium which is able to record the measurement results, the calculation results, and a program. Examples thereof include a semiconductor memory, an IC card, an optical disc, a magnetic disk, a magneto-optical disc, a magnetic tape, a digital video disk, and the like. The program recorded in the storage unit enables the computer to configure the method for setting polymerization condition of the present embodiment.

The physical property acquiring unit 120 acquires a physical property value a derived from a functional group before heating of the polymerization-reactive compound and a physical property value b derived from a remaining functional group after maintaining a temperature for a predetermined time in a case of heating a composition including a polymerization-reactive compound and a polymerization catalyst and/or a polymerization initiator and retaining heat at a predetermined temperature. The remaining functional group ratio calculating unit 140 calculates a remaining functional group ratio from the physical property value a and the physical property value b. The reaction rate coefficient calculating unit 160 calculates a reaction rate coefficient from the remaining functional group ratio on the basis of a reaction rate equation. The polymerization temperature calculating unit 180 calculates a polymerization temperature on the basis of the reaction rate coefficient and conditions below.

Conditions: In a range of 10% or more and 80% or less of a polymerization ratio, a polymerization rate is 0.4%/hr or more and 15%/hr or less, and a standard deviation is 2.3%/hr or less.

A detailed description will be given below.

The physical property acquiring unit 120 acquires the physical property value a derived from a functional group before heating of the polymerization-reactive compound and the physical property value b derived from a remaining functional group after retaining heat at a predetermined temperature for a predetermined time in a case of heating the composition and retaining heat at a predetermined temperature, for example, from the storage unit 100 (physical property acquiring step S10).

The temperature at which the polymerization-reactive compound is heated varies depending on the temperature at which the polymerization-reactive compound is polymerized and, for example, it is possible to select one or more temperatures from a range of 5° C. or higher and 140° C. or lower. The temperature maintenance time depends on the temperature being maintained and is not particularly limited as long as the polymerization is not completed.

In a composition formed of a combination of the polymerization-reactive compound and a polymerization catalyst, and/or a polymerization initiator described above, the storage unit 100 stores the physical property value a derived from a functional group before heating of the polymerization-reactive compound and the physical property value b derived from the remaining functional group after retaining heat at a predetermined temperature for a predetermined time. The physical property value b is stored in association with the heat maintenance temperature (the temperature after heating) and exists for at least one period of elapsed time for each of plural heat maintenance temperatures. The physical property values a and b are directly input to the storage unit 100 from an input unit (not shown). The stored physical property values are the heat value, the specific gravity, the weight-average molecular weight, the number-average molecular weight, the spectral intensity in IR measurement, the $^1$H-NMR spectral intensity, or the $^{13}$C-NMR spectral intensity.

The physical property acquiring unit 120 is able to read and acquire the physical property value a and the physical property value b stored in the storage unit 100, for example. It is also possible for the physical property values a and b obtained by measuring devices such as a thermal analyzer, a specific gravity measuring device, a GPC measuring device, an IR measuring device, and an NMR device to be directly input to the physical property acquiring unit 120 from an input unit (not shown).

Specific examples of a thermal analyzer able to be used in the present embodiment include a differential scanning calorimeter, a calorimeter, a microcalorimeter, a differential thermal analyzer, a differential simultaneous thermo-gravimeteric analyzer, a thermogravimetric analyzer, a thermomechanical measuring device, a dynamic thermomechanical measuring device, and the like.

Next, the remaining functional group ratio calculating unit 140 acquires the physical property value a and the physical property value b from the physical property acquiring unit 120 and calculates the remaining functional group ratio on the basis of these physical property values (remaining functional group ratio calculating step S20).

A description will be given below of a case where the remaining functional group ratio calculating unit 140 calculates the remaining functional group ratio according to, for example, the amount of heat measured by thermal analysis.

It is possible to represent the remaining functional group ratio by the following Equation 1.

$$\text{Remaining functional group ratio} = Xt/X_0 \quad \text{Equation 1:}$$

$X_0$ (J/g): Amount of heat measured by DSC thermal analysis of the prepared solution immediately after preparation (before polymerization)

$Xt$ (J/g): Amount of heat of the prepared solution after temperature maintenance at a specific temperature for t hours In the present embodiment, $X_0$ corresponds to the physical property value a and $Xt$ corresponds to the physical property value b.

For example, in a case of calculating the remaining functional group ratio on the basis of the specific gravity, it is possible to represent the remaining functional group ratio by Equation 2.

$$\text{Remaining functional group ratio} = [1-[(\text{specific gravity measured after temperature maintenance at a specific temperature for } t \text{ hours-specific gravity of prepared solution immediately after preparation (before heating)})/\Delta d]] \quad \text{Equation 2:}$$

$\Delta d$ (increase amount in specific gravity for each 1% decrease in remaining functional groups) = [(specific gravity of cured resin-specific gravity of liquid immediately after preparation)/100

In the present embodiment, the specific gravity of the prepared solution immediately after the preparation (before heating) corresponds to the physical property value a, while the specific gravity measured after temperature maintenance at a specific temperature for t hours corresponds to the physical property value b.

In addition, with an IR measurement device, in a case where a (thio)urethane resin is used as a polymerization-reactive compound, it is possible to calculate the remaining functional group ratio by quantifying the change over time in the ratio of the spectral intensity of the NCO group and the CH group.

The reaction rate coefficient calculating unit 160 acquires the remaining functional group ratio from the remaining functional group ratio calculating unit 140, performs a reaction rate theoretical analysis on the remaining functional group ratio on the basis of the reaction rate equation, and calculates the reaction rate coefficient (reaction rate coefficient calculating step S30).

The reaction rate coefficient calculating unit 160 is able to read a reaction rate equation stored in the storage unit 100 in advance.

Examples of reaction rate equations include an nth-order reaction rate equation (n is 0 or more), a Prout-Tompkins rate equation, a Bawn rate equation, a Leeson-Mattocks rate equation, and the like. The reaction rate coefficient calculating unit 160 is able to select an optimal equation on the basis of the polymerizable composition and the order of the reaction.

The reaction rate coefficient calculating unit 160 calculates a reaction rate coefficient on the basis of the reaction rate equation read from the storage unit 100 and on the basis of the remaining functional group ratio acquired from the remaining functional group ratio calculating unit 140. A description will be given below of a case where the n-th order reaction rate equation represented by Equation 3 is used.

$$kt = f(\text{remaining functional group ratio}) \quad \text{Equation 3:}$$

k: nth order reaction rate coefficient (n is a real number which is 0 or more)

t: Temperature maintenance time f (remaining functional group ratio) is determined by the value of n with a function of the remaining functional group ratio.

In a graph in which the horizontal axis represents the temperature maintenance time t and the vertical axis represents f (remaining functional group ratio) into which the remaining functional group ratio of the target substance (polymerizable compound) in the sample is substituted, the reaction rate coefficient calculating unit 160 plots the remaining functional group ratio for each temperature maintenance time. The reaction rate coefficient calculating unit 160 acquires a regression line from the graph and acquires the slope of the regression line as the reaction rate coefficient k.

To determine the correlation relationship between the reaction rate coefficient of the change in the polymerizable compound included in the sample and the temperature of the sample, for example, with the temperature of the sample when the temperature is maintained being converted to the absolute temperature T and the reciprocal thereof on the horizontal axis and the natural logarithm of the reaction rate coefficient k at this temperature on the vertical axis, each point is plotted to obtain a regression line having a slope of ($-Ea/R$). This plot is called an Arrhenius plot.

Specifically, in a graph in which the vertical axis is Ln (k) and the horizontal axis is the reciprocal of the absolute temperature, the reaction rate coefficient calculating unit 160 determines Ln (k) on the basis of the obtained reaction rate coefficient and creates an Arrhenius plot by plotting in the table. From the Arrhenius plot, a regression line and a regression line equation of Equation 4 are obtained.

$$y = ax + b (\text{regression line}) \quad \text{Equation 4:}$$

To predict the remaining functional group ratio, for example, the reciprocal of the desired absolute temperature T is substituted into the regression line determined as described above to calculate the reaction rate coefficient k at the absolute temperature T and, by substituting this reaction rate coefficient into the reaction rate equation illustrated in Equation 3 determined as described above, the remaining functional group ratio in a case where the sample is placed at the absolute temperature T for t hours is calculated.

Specifically, the reaction rate coefficient calculating unit 160 obtains Equation 5 by replacing y, a, x, and b in the regression line of Equation 4 with the following.

$y = \text{Ln}(k)$
$a = (-Ea/R)$
$x = (1/T)$
$b = \text{Ln (frequency factor)}$
Ea: Activation energy (J mol$^{-1}$K$^{1}$)
R: Gas coefficient (8.3145 J mol$^{-1}$)
T: Absolute temperature
A: Frequency factor $$\text{Ln}(k) = (-Ea/R) \times (1/T) + \text{Ln}(A) \quad \text{Equation 5:}$$

The reaction rate coefficient calculating unit 160 further obtains Equation 6 and calculates the reaction rate coefficient at the temperature used as the polymerization temperature using the Equation 5 and Equation 6.

$$k = \text{EXP}(y) \quad \text{Equation 6:}$$

The reaction rate coefficient calculating unit 160 is also able to calculate the polymerization ratio from Equation (7).

$$\text{polymerization ratio (\%)} = (1 - \text{remaining functional group ratio}) \times 100 \quad \text{Equation 7:}$$

The polymerization temperature calculating unit 180 acquires the reaction rate coefficient from the reaction rate coefficient calculating unit 160 and calculates the polymerization temperature on the basis of the following polymerization conditions (polymerization temperature calculating step S40).

(Polymerization Conditions)

At a polymerization ratio of 10% or more and 80% or less, the polymerization rate is 0.4%/hr or more and 15%/hr or less and the standard deviation of the polymerization rate (slope) every hour is 2.3%/hr or less.

By calculating the polymerization temperature for each polymerization time on the basis of the polymerization conditions, the polymerization ratio of the optical material is increased, it is possible to suppress variations in the temperature distribution during the polymerization of the polymerizable composition, and it is possible to prevent the occurrence of optical distortion and striae in the optical material as a result.

In the storage unit 100, desired polymerization conditions in a range of a polymerization ratio of 10% or more and 80% or less are stored in advance by a user. Specifically, the storage unit 100 stores a desired polymerization rate and standard deviation of the polymerization rate in advance. It is also possible to directly input to the polymerization temperature calculating unit 180 from an input unit (not shown).

The polymerization temperature calculating unit 180 acquires the reaction rate coefficient from the reaction rate coefficient calculating unit 160 and acquires the desired polymerization conditions from the storage unit 100. The reaction rate coefficient is associated with the type of the polymerizable compound and the polymerization temperature calculating unit 180 selects a first-order reaction rate equation or a second-order reaction rate equation on the basis of the type of the polymerizable compound. Then, the polymerization temperature calculating unit 180 performs a back calculation using the selected reaction rate equation and calculates the polymerization temperature condition for each polymerization time, so as to satisfy the desired polymerization conditions acquired from the storage unit 100.

The polymerization temperature calculating unit 180 also acquires the polymerization ratio from the reaction rate coefficient calculating unit 160 and the polymerization temperature calculating unit 180 transmits the polymerization temperature conditions for each polymerization time and the polymerization ratio to be stored in the storage unit 100.

The polymerization temperature calculating unit 180 may be configured so as to be able to output the polymerization temperature for each polymerization time and the polymerization ratio to a monitor (not shown) or the like. Due to this, it is possible for the user to check the polymerization temperature and the polymerization ratio for each polymerization time and to carry out the polymerization reaction according to these conditions.

The apparatus for manufacturing optical material of the present embodiment is provided with the apparatus for setting polymerization condition described above.

Specifically, the apparatus for manufacturing optical material of the present embodiment is provided with:

a heating unit for heating a composition including a polymerization-reactive compound and a polymerization catalyst and/or a polymerization initiator;

the apparatus for setting polymerization condition 10 of the present embodiment; and a control unit for controlling the heating unit so as to heat the composition including a polymerization-reactive compound and a polymerization catalyst and/or a polymerization initiator on the basis of polymerization temperature conditions obtained by the apparatus for setting polymerization condition 10.

The heating unit is a device which is able to heat a mold filled with a composition and examples of heating furnaces include an electric furnace, a hot-air circulation furnace, an infrared oven, a microwave oven, and the like.

The control unit may be installed integrally with or separately from the heating furnace and may be provided with a unit for measuring an amount of heat (for example, measurement of the temperature distribution in the oven, the outer surface temperature of the mold, the inner surface temperature of the mold, and the temperature in the polymerizing step until the composition is cured) and a monitor. Furthermore, the control unit is configured so as to be able to access the storage unit 100 of the apparatus for setting polymerization condition 10 and also to monitor the temperature of the heating unit.

After the start of the polymerization, the control unit monitors the temperature of the polymerization composition, compares the temperature with the polymerization temperature conditions for each polymerization time obtained from the storage unit 100, and controls the heating unit on the basis of the polymerization temperature conditions.

The apparatus for manufacturing optical material of the present embodiment is able to suitably execute the method for setting polymerization condition of the present embodiment.

Embodiments of the present invention were described above with reference to the drawings; however, the above are merely examples of the present invention and it is also possible to adopt various other configurations.

EXAMPLES

A more detailed description will be given below of the present invention with reference to Examples, but the present invention is not limited thereto.

The following components were used in Examples and Comparative Examples.

Allyl carbonate composition 1: RAV 7MC (poly(allyl carbonate) compound of diethylene glycol, neopentyl glycol and pentaerythritol and an oligomer thereof, manufactured by Acomon)

<Ultraviolet Absorber>

Eversorb 109: Benzotriazole-based ultraviolet absorber, manufactured by Everlight Chemical Industrial Corp.

Tinuvin-326: Benzotriazole-based ultraviolet absorber manufactured by BASF

Viosorb-583: Benzotriazole-based ultraviolet absorber manufactured by Kyodo Chemical Co., Ltd.

<Radical Polymerization Initiator>

Luperox 531M80: Peroxyketal-based radical polymerization initiator manufactured by ARKEMA Yoshitomi Ltd.

<Other Additives>

Additive 1: Polypropylene glycol, diol type, 2000 (manufactured by Wako Pure Chemical Industries, Ltd.)

Example 1

To 58.9 parts by weight of an isocyanate composition (manufactured by Evonic) including dicyclohexylmethane 4,4'-diisocyanate, 1.5 parts by weight of an ultraviolet absorber Eversorb 109, 0.64 parts by weight of Tinuvin-326, and 0.18 parts by weight of dibutyltin dichloride as a catalyst were added, 0.15 parts by weight of an internal release agent for MR (manufactured by Mitsui Chemicals, Inc.) as an internal release agent were added thereto, and the mixture was rapidly stirred and dissolved. Furthermore, 41.1 parts by weight of a thiol composition including 5,7-dimercaptomethyl-1,11-dimercapto-3,6,9-trithiaundecane, 4,7-dimercaptomethyl-1,11-dimercapto-3,6,9-trithiaundecane and 4,8-dimercaptomethyl-1,11-dimercapto-3,6,9-trithiaundecane were added thereto and the mixture was rapidly mixed and stirred at 15° C. Approximately 0.5 g of the stirred solution was placed as two samples (for two test temperatures) in sample bottles and rapidly depressurized and degassed by a vacuum pump. The reduced pressure was returned to atmospheric pressure. The heat value of the sample immediately after the preparation was measured using a differential scanning calorimeter as a reaction time of zero hours. The sample bottles of the two samples were subjected to nitrogen substitution and analysis was performed by a differential scanning calorimeter three times at 30° C. for each elapsed time (after 0 hours, after 3 hours, and after 25 hours) and two times at 70° C. for each elapsed time (after 0 hours and after 3 hours) to obtain heat values.

Heat value after 0 hours at 30° C.: 203.3 (J/g)
Heat value after 3 hours at 30° C.: 193.3 (J/g)
Heat value after 25 hours at 30° C.: 142.3 (J/g)
Heat value after 0 hours at 70° C.: 203.3 (J/g)
Heat value after 3 hours at 70° C.: 134.1 (J/g)

The heat values described above were directly input and stored in the storage unit 100 and the polymerization temperature condition was calculated by the apparatus for setting polymerization condition 10 of the present embodiment.

In the remaining functional group ratio calculating unit 140, results were obtained in which at 30° C., the remaining functional group ratio immediately after mixing and stirring was 1.0000, the remaining functional group ratio after 3 hours was 0.9498, and the remaining functional group ratio after 25 hours was 0.7000, and, at 70° C., the remaining functional group ratio immediately after mixing and stirring was 1.0000 and the remaining functional group ratio after 3 hours was 0.6596.

The reaction rate coefficient calculating unit 160 used a second-order reaction rate equation and the reaction rate coefficient, which is the slope of the regression line, was 0.017 at 30° C. and 0.172 at 70° C.

Figure 3:
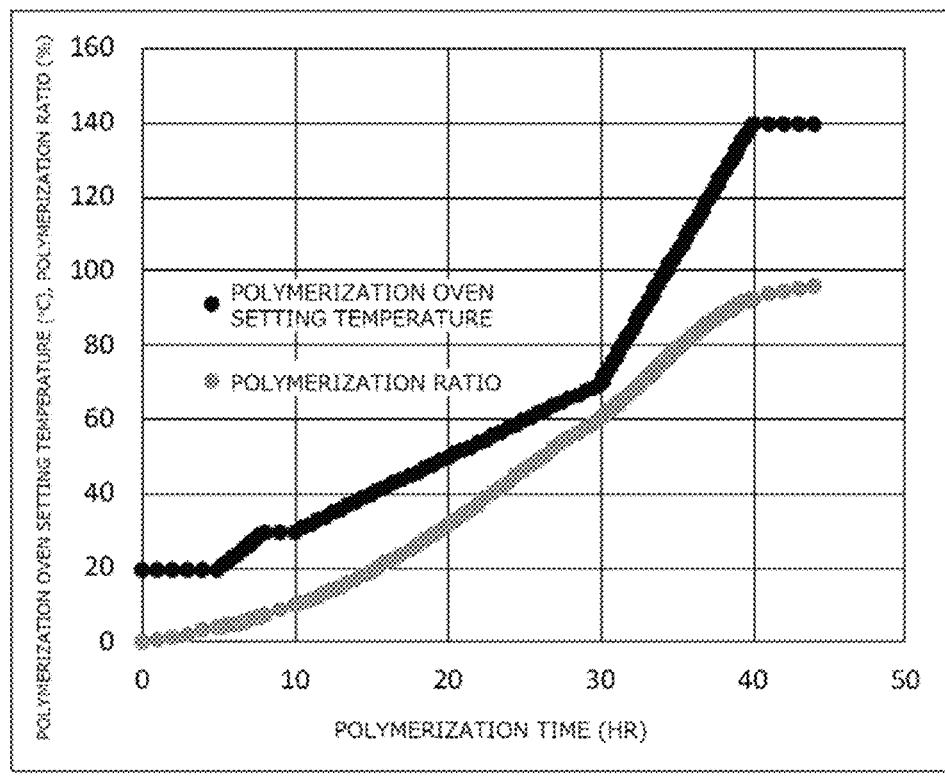
FIG. 3 is a chart in which a polymerization temperature condition for each polymerization time obtained by the method for setting polymerization condition, a polymerization time, and a polymerization ratio are plotted in Example 1.

In the storage unit 100, polymerization conditions were stored in which the slope (polymerization rate) of the polymerization ratio from 10% to 80% was 2.70%/hr (average value) and the standard deviation of the polymerization rate (slope) every hour was 0.69%/hr. The polymerization temperature calculating unit 180 accessed the polymerization conditions stored in the storage unit 100 and calculated the polymerization temperature conditions for each polymerization time. FIG. 3 shows a chart in which polymerization temperature conditions for each polymerization time, a polymerization time, and a polymerization ratio, which are displayed on a monitor (not shown), are plotted.

Example 2

Polymerization was carried out under the temperature conditions obtained in Example 1.

To 589 parts by weight of a composition (manufactured by Evonic) including an isomer, which is main component of which is dicyclohexylmethane 4,4'-diisocyanate as a raw material, 15 parts by weight of an ultraviolet absorber Eversorb 109, 6.4 parts by weight of Tinuvin-326, and 1.8 parts by weight of dibutyltin dichloride as a catalyst were added, 1.5 parts by weight of an internal release agent for MR (manufactured by Mitsui Chemicals, Inc.) as an internal release agent were added thereto, and mixing and stirring were carried out at 15° C. to 25° C. to dissolve the mixture. To the mixture, 411 parts by weight of a composition including 5,7-dimercaptomethyl-1,11-dimercapto-3,6,9-trithiaundecane, 4,7-dimercaptomethyl-1,11-dimercapto-3,6,9-trithiaundecane and 4,8-dimercaptomethyl-1,11-dimercapto-3,6,9-trithiaundecane were further added and mixing and stirring were carried out at 15° C. to 25° C. Thereafter, filtration was carried out to purify the mixture and the solution was depressurized and degassed by a vacuum pump. This solution was cast in a glass mold to create 10 samples. The above was carried out in a mold shape of 081 mm, in which the front surface had 2 curves, the back surface had 6 curves, and the center thickness was thick at 15.6 mm.

Polymerization was performed by the apparatus for manufacturing optical material of the present embodiment. The temperature of the polymerization oven was set on the basis of the temperature conditions obtained in Example 1 and the temperature conditions were controlled. After the completion of the polymerization (polymerization ratio: 96.4%), a cured polythiourethane resin was obtained from the polymerization oven after cooling. After removing internal stress by an annealing treatment, the obtained resin was evaluated for optical distortion by a high-pressure mercury lamp and, as a result, in 10 out of 10 samples, lenses were obtained which did not have optical distortion and which were extremely excellent for optical applications.

Example 3

To 50.6 parts by weight of m-xylylene diisocyanate, 1.5 parts by weight of an ultraviolet absorber Viosorb-583 and 0.008 parts by weight of dibutyltin dichloride were added, 0.18 parts by weight of an internal release agent for MR as an internal release agent (manufactured by Mitsui Chemicals, Inc.) were added thereto, and mixing and stirring were carried out at 15° C. to dissolve the mixture. To the mixture, 49.4 parts by weight of a composition including 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane were further added and the mixture was rapidly mixed and stirred at 15° C. Approximately 0.5 g of the stirred solution was placed as two samples (for two test temperatures) in sample bottles and rapidly depressurized and degassed by a vacuum pump. The reduced pressure was returned to atmospheric pressure. The heat value of the sample immediately after the preparation was measured using a differential scanning calorimeter as a reaction time of zero hours. The sample bottles of the two samples were subjected to nitrogen substitution and analysis was performed by a differential scanning calorimeter five times at 30° C. (after 0 hours, after 1 hour, after 4 hours, after 24 hours, and after 48 hours) and two times at 70° C. (after 0 hours and after 3 hours) to obtain heat values.

Heat value after 0 hours at 30° C.: 279.3 (J/g)
Heat value after 1 hour at 30° C.: 278.2 (J/g)
Heat value after 4 hours at 30° C.: 229.3 (J/g)
Heat value after 24 hours at 30° C.: 94.0 (J/g)
Heat value after 48 hours at 30° C.: 63.9 (J/g)
Heat value after 0 hours at 70° C.: 279.3 (J/g)
Heat value after 3 hours at 70° C.: 93.2 (J/g)

The heat values described above were directly input and stored in the storage unit 100 and the polymerization temperature condition was calculated by the apparatus for setting polymerization condition 10 of the present embodiment.

In the remaining functional group ratio calculating unit 140, results were obtained in which at 30° C., the remaining functional group ratio immediately after mixing and stirring was 1.0000, the remaining functional group ratio after 1 hour was 0.9961, the remaining functional group ratio after 4 hours was 0.8210, the remaining functional group ratio after 24 hours was 0.3366, and the remaining functional group ratio after 48 hours was 0.2288. At 70° C., results were obtained in which the remaining functional group ratio immediately after mixing and stirring was 1.0000 and the remaining functional group ratio after 3 hours was 0.3337.

The reaction rate coefficient calculating unit 160 used a second-order reaction rate equation and the reaction rate coefficient, which is the slope of the regression line, was 0.0784 at 30° C. and 0.6656 at 70° C.

Figure 4:
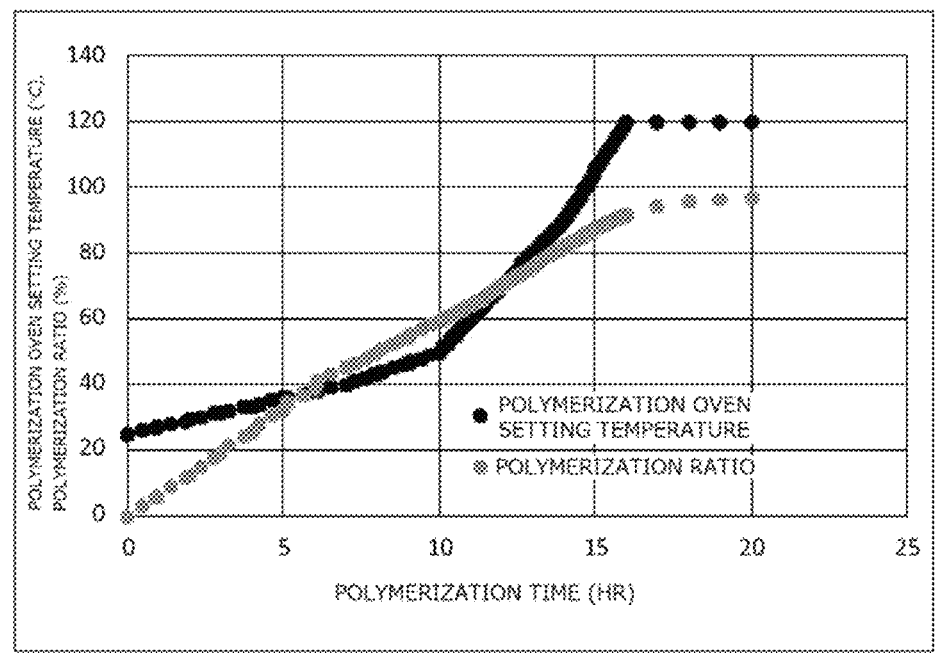
FIG. 4 is a chart in which a polymerization temperature condition for each polymerization time obtained by the method for setting polymerization condition, a polymerization time, and a polymerization ratio are plotted in Example 3.

In the storage unit 100, polymerization conditions were stored in which the slope (polymerization rate) of the polymerization ratio from 10% to 80% was 5.85%/hr (average value) and the standard deviation of the polymerization rate (slope) every hour was 0.78%/hr. The polymerization temperature calculating unit 180 accessed the polymerization conditions stored in the storage unit 100 and calculated the polymerization temperature conditions for each polymerization time. FIG. 4 shows a chart in which polymerization temperature conditions for each polymerization time, a polymerization time and a polymerization ratio, which are displayed on a monitor (not shown), are plotted.

Example 4

Polymerization was carried out under the temperature conditions obtained in Example 3.

To 506 parts by weight of m-xylylene diisocyanate, 15 parts by weight of an ultraviolet absorber Viosorb-583 and 0.08 parts by weight of dibutyltin dichloride were added, 1.8 parts by weight of an internal release agent for MR (manufactured by Mitsui Chemicals, Inc.) as an internal release agent were added thereto and mixing and stirring were carried out at 15° C. to 25° C. to dissolve the mixture. To the mixture, 494 parts by weight of a composition including 5,7-dimercaptomethyl-1,11-dimercapto-3,6,9-trithiaundecane, 4,7-dimercaptomethyl-1,11-dimercapto-3,6,9-trithiaundecane and 4,8-dimercaptomethyl-1,11-dimercapto-3,6,9-trithiaundecane were further added and mixing and stirring were carried out at 15° C. to 25° C. Thereafter, filtration was carried out to purify the mixture and the solution was depressurized and degassed by a vacuum pump. This solution was cast in a glass mold to create 10 samples. The above was carried out in a mold shape of 081 mm, in which the front surface had 4 curves, the back surface had 4 curves, and the center thickness was thin at 2.5 mm.

Polymerization was performed by the apparatus for manufacturing optical material of the present embodiment. The temperature of the polymerization oven was set on the basis of the temperature conditions obtained in Example 3 and the temperature conditions were controlled. After the completion of the polymerization (polymerization ratio: 97.0%), a cured resin was obtained from the polymerization oven after cooling. After removing internal stress by an annealing treatment, the obtained resin was evaluated for optical distortion by a high-pressure mercury lamp and, in 10 out of 10 samples, lenses were obtained which did not have optical distortion and which were extremely excellent for optical applications.

Example 5

Figure 5:
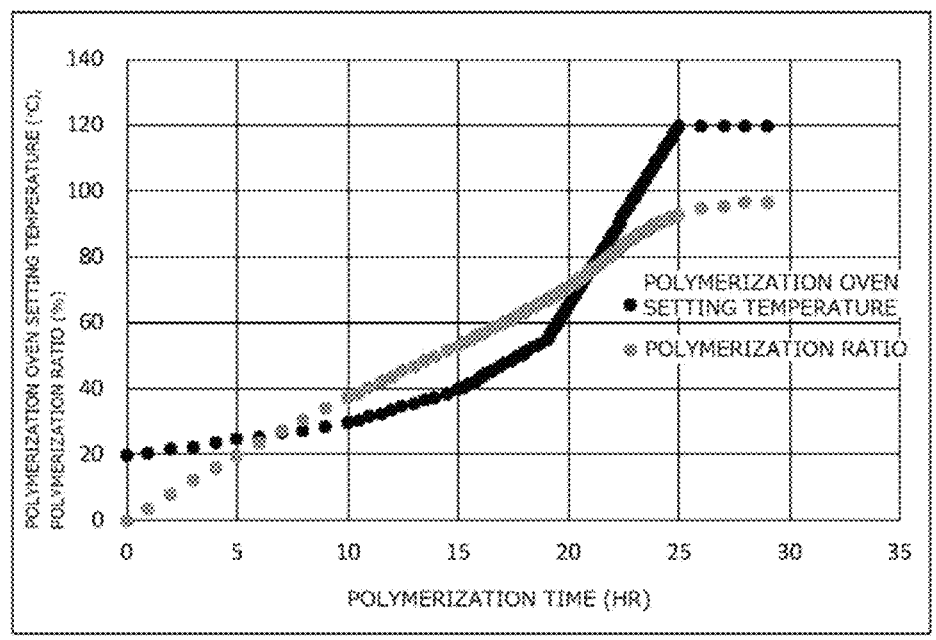
FIG. 5 is a chart in which a polymerization temperature condition for each polymerization time obtained by the method for setting polymerization condition, a polymerization time, and a polymerization ratio are plotted in Example 5.

The same process as in Example 3 was performed, except that temperature conditions were created where the slope (polymerization rate) of the polymerization ratio from 10% to 80% was 3.65%/hr (average value) and the standard deviation of the polymerization rate (slope) every hour was 0.56%/hr. FIG. 5 shows a chart in which polymerization temperature conditions for each polymerization time, a polymerization time, and a polymerization ratio, which are displayed on a monitor (not shown), are plotted.

Example 6

Polymerization was performed under the temperature conditions obtained in Example 5.

To 506 parts by weight of m-xylylene diisocyanate, 15 parts by weight of an ultraviolet absorber Viosorb-583 and 0.08 parts by weight of dibutyltin dichloride were added, 1.8 parts by weight of an internal release agent for MR (manufactured by Mitsui Chemicals, Inc.) as an internal release agent were added thereto, and mixing and stirring were carried out at 15° C. to 25° C. to dissolve the mixture.

To the mixture, 494 parts by weight of a composition including 5,7-dimercaptomethyl-1,11-dimercapto-3,6,9-trithiaundecane, 4,7-dimercaptomethyl-1,11-dimercapto-3,6,9-trithiaundecane and 4,8-dimercaptomethyl-1,11-dimercapto-3,6,9-trithiaundecane were further added and mixing and stirring were carried out at 15° C. to 25° C. Thereafter, filtration was carried out to purify the mixture and the solution was depressurized and degassed by a vacuum pump. This solution was cast in a glass mold to create 10 samples. The above was carried out in a mold shape of ⌀80 mm, in which the front surface had 2 curves, the back surface had 6 curves, and the center thickness was thick at 15.6 mm.

Polymerization was performed by the apparatus for manufacturing optical material of the present embodiment. The temperature of the polymerization oven was set on the basis of the temperature conditions obtained in Example 5 and the temperature conditions were controlled. After the completion of the polymerization (polymerization ratio: 97.1%), a cured resin was obtained from the polymerization oven after cooling. After removing internal stress by an annealing treatment, the obtained resin was evaluated for optical distortion by a high-pressure mercury lamp and, in 10 out of 10 samples, lenses were obtained which did not have optical distortion and which were extremely excellent for optical applications.

Example 7

To 99.2 parts by weight of RAV 7MC, 0.8 parts by weight of Luperox 531M80 as a radical polymerization initiator and 0.05 parts by weight of polypropylene glycol, diol type, 2000 (manufactured by Wako Pure Chemical Industries, Ltd.) were added, followed by rapid stirring and mixing. Approximately 0.5 g of the stirred solution was placed as two samples (for two test temperatures) in sample bottles and rapidly depressurized and degassed by a vacuum pump. The reduced pressure was returned to atmospheric pressure using nitrogen. The heat value of the sample immediately after the preparation was measured using a differential scanning calorimeter as a reaction time of zero hours. The sample bottles of the two samples were subjected to nitrogen substitution and analysis was performed by a differential scanning calorimeter four times at 80° C. (after 0 hours, after 5 hours, after 30 hours, and after 35 hours) and three times at 100° C. (after 0 hours, after 2 hours, and after 5 hours) to obtain heat values.

Heat value after 0 hours at 80° C.: 358.6 (J/g)
Heat value after 5 hours at 80° C.: 324.0 (J/g)
Heat value after 30 hours at 80° C.: 198.6 (J/g)
Heat value after 35 hours at 80° C.: 183.2 (J/g)
Heat value after 0 hours at 100° C.: 358.6 (J/g)
Heat value after 2 hours at 100° C.: 221.1 (J/g)
Heat value after 5 hours at 100° C.: 174.1 (J/g)

The heat values described above were directly input and stored in the storage unit 100 and the polymerization temperature condition was calculated by the apparatus for setting polymerization condition 10 of the present embodiment.

In the remaining functional group ratio calculating unit 140, results were obtained in which at 80° C., the remaining functional group ratio immediately after mixing and stirring was 1.0000, the remaining functional group ratio after 5 hours was 0.9035, the remaining functional group ratio after 30 hours was 0.5537, and the remaining functional group ratio after 35 hours was 0.5100. At 100° C., the remaining functional group ratio immediately after mixing and stirring was 1.0000, the remaining functional group ratio after 2 hours was 0.6166, and the remaining functional group ratio after 5 hours was 0.4854.

The reaction rate coefficient calculating unit 160 used a first-order reaction rate equation and the reaction rate coefficient, which is the slope of the regression line, was 0.0194 at 80° C. and 0.158 at 100° C.

Figure 6:
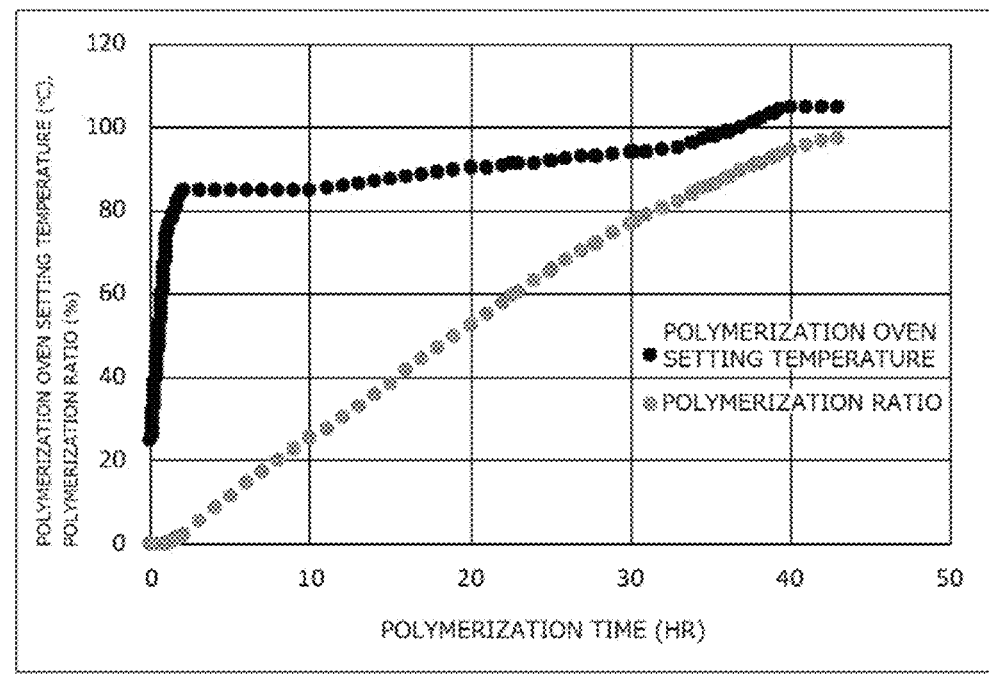
FIG. 6 is a chart in which a polymerization temperature condition for each polymerization time obtained by the method for setting polymerization condition, a polymerization time, and a polymerization ratio are plotted in Example 7.

In the storage unit 100, polymerization conditions were stored in which the slope (polymerization rate) of the polymerization ratio from 10% to 80% was 2.57%/hr (average value) and the standard deviation of the polymerization rate (slope) every hour was 0.26%/hr. The polymerization temperature calculating unit 180 accessed the polymerization conditions stored in the storage unit 100 and calculated the polymerization temperature conditions for each polymerization time. FIG. 6 shows a chart in which polymerization temperature conditions for each polymerization time, a polymerization time, and a polymerization ratio, which are displayed on a monitor (not shown), are plotted.

Example 8

To 992 parts by weight of RAV 7MC, 8 parts by weight of Luperox 531M80 as a radical polymerization initiator and 0.50 parts by weight of polypropylene glycol, diol type, 2000 (manufactured by Wako Pure Chemical Industries, Ltd.) were added, followed by stirring and mixing. The result was purified by filtration, degassed under reduced pressure, and then cast. There were two types of cast mold shapes used and the mold shape 1 was ⌀81 mm, in which the front surface had 2 curves, the back surface had 6 curves, and the center thickness was thick at 10 mm and the mold shape 2 was ⌀81 mm, in which the front surface had 4 curves, the back surface had 4 curves, and the center thickness was thin at 2 mm and 10 samples were cast with each. The temperature of the polymerization oven was set on the basis of the temperature conditions obtained in Example 7. After the polymerization was completed (polymerization ratio: 97.4%), the mixture was cooled to 60° C. and the molded product was released from the mold. The lenses molded in mold shape 1 and mold shape 2 did not have cracks generated therein when cured and had good release properties. No cracks were generated at the time of mold release. Lenses without any optical distortion and extremely excellent for optical applications were obtained.

Example 9

Figure 7:
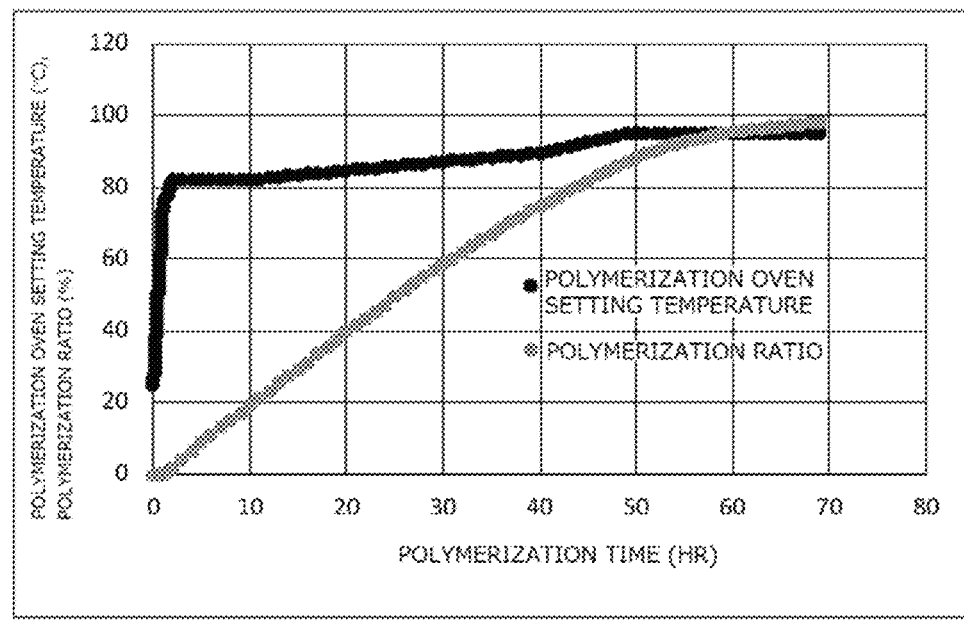
FIG. 7 is a chart in which a polymerization temperature condition for each polymerization time obtained by the method for setting polymerization condition, a polymerization time, and a polymerization ratio are plotted in Example 9.

The same process as in Example 7 was performed, except that temperature conditions were created where the slope (polymerization rate) from a polymerization ratio of 10% to 80% was 1.83%/hr (average value) and the standard deviation of the polymerization rate (slope) every hour was 0.26%/hr. FIG. 7 shows a chart in which polymerization temperature conditions for each polymerization time, a polymerization time and a polymerization ratio, which are displayed on a monitor (not shown), are plotted.

Example 10

Polymerization was performed under the temperature conditions obtained in Example 9.

To 992 parts by weight of RAV 7MC, 8 parts by weight of Luperox 531M80 as a radical polymerization initiator and 0.50 parts by weight of polypropylene glycol, diol type, 2000 (manufactured by Wako Pure Chemical Industries, Ltd.) were added, followed by stirring and mixing. The result was purified by filtration, degassed under reduced pressure, and then cast. There were two types of cast mold shapes used and the mold shape 1 was ⌀81 mm, in which the front surface had 2 curves, the back surface had 6 curves, and the center thickness was thick at 10 mm and the mold shape 2 was ⌀81 mm, in which the front surface had 2 curves, the back surface had 6 curves, and the center thickness was thin at 2 mm and 10 samples were cast with each. The cast mold was placed in a polymerization oven and polymerization was performed using the created polymerization temperature conditions.

Polymerization was performed by the apparatus for manufacturing optical material of the present embodiment. The temperature of the polymerization oven was set on the basis of the temperature conditions obtained in Example 8 and the temperature conditions were controlled. After the polymerization was completed (polymerization ratio: 98.1%), the mixture was cooled to 60° C. and the molded product was released from the mold. Lenses of each 10 samples molded in mold shape 1 and mold shape 2 did not have cracks generated therein when cured and had good mold release properties. No cracks were generated at the time of mold release. Lenses without any optical distortion and extremely excellent for optical applications were obtained.

Example 11

50.76 parts by weight of a mixture of 2,5-bis(isothiocyanatomethyl) bicyclo-[2.2.1]-heptane and 2,6-bis(isothiocyanatomethyl) bicyclo-[2.2.1]-heptane was stirred under a nitrogen atmosphere while maintaining the temperature at 15° C. and 0.33 parts by weight of ethylenediamine was dropped therein at a constant rate over 2 hours using a micro syringe. Thereafter, the mixture was further aged at 15° C. for 1 hour to obtain a reaction solution. To the reaction solution, 0.05 parts by weight of dibutyltin dichloride were added, 0.23 parts by weight of an internal release agent for MR (manufactured by Mitsui Chemicals, Inc.) as an internal release agent were added thereto, and stirring was carried out to dissolve the mixture. Furthermore, 41.54 parts by weight of 4-mercaptomethyl-1,8-dimercapto-3,6-dithiaoctane were added thereto and the mixture was rapidly mixed and stirred at 15° C. Approximately 0.5 g of the stirred solution was placed as two samples (for two test temperatures) in sample bottles and rapidly depressurized and degassed by a vacuum pump. The reduced pressure was returned to atmospheric pressure. The heat value of the sample immediately after the preparation was measured using a differential scanning calorimeter as a reaction time of zero hours. The sample bottles of the two samples were subjected to nitrogen substitution and analysis was performed by a differential scanning calorimeter three times at 15° C. for each elapsed time (after 0 hours, after 25 hours, and after 48 hours) and three times at 50° C. for each elapsed time (after 0 hours, after 2 hours, and after 5 hours) to obtain heat values.

Heat value after 0 hours at 15° C.: 365.64 (J/g)
Heat value after 25 hours at 15° C.: 342.09 (J/g)
Heat value after 48 hours at 15° C.: 318.93 (J/g)
Heat value after 0 hours at 50° C.: 365.64 (J/g)
Heat value after 2 hours at 50° C.: 326.06 (J/g)
Heat value after 5 hours at 50° C.: 263.49 (J/g) The heat values described above were directly input and stored in the storage unit 100 and the polymerization temperature condition was calculated by the apparatus for setting polymerization condition 10 of the present embodiment.

In the remaining functional group ratio calculating unit 140, results were obtained in which, at 15° C., the remaining functional group ratio immediately after mixing and stirring was 1.0000, the remaining functional group ratio after 25 hours was 0.9356, and the remaining functional group ratio after 48 hours was 0.8723, and, at 50° C., the remaining functional group ratio immediately after mixing and stirring was 1.0000, the remaining functional group ratio after 2 hours was 0.8918, and the remaining functional group ratio after 5 hours was 0.7206.

The reaction rate coefficient calculating unit 160 used a second-order reaction rate equation and the reaction rate coefficient, which is the slope of the regression line, was 0.003 at 15° C. and 0.0784 at 50° C.

Figure 8:
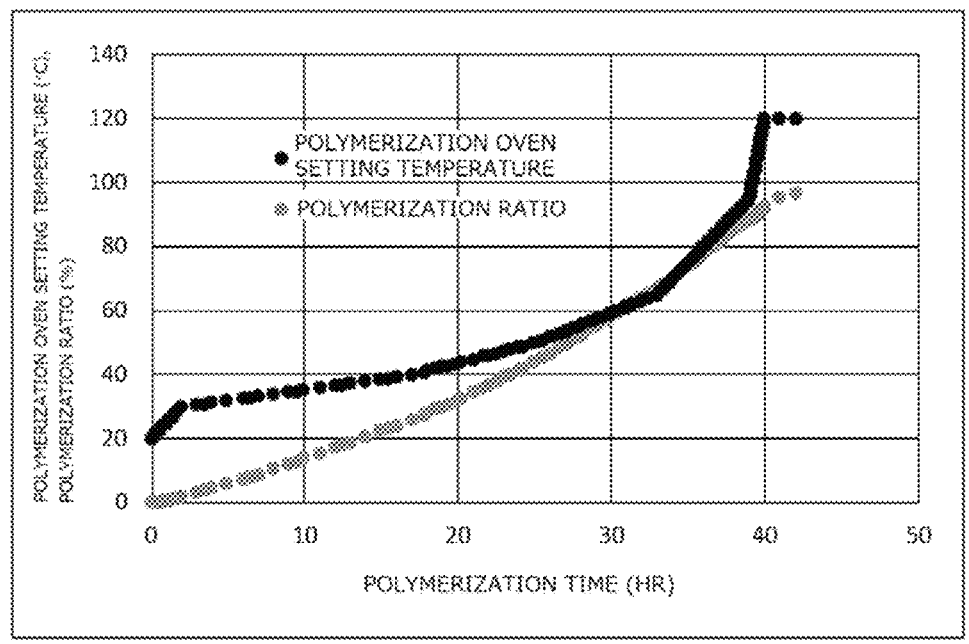
FIG. 8 is a chart in which a polymerization temperature condition for each polymerization time obtained by the method for setting polymerization condition, a polymerization time, and a polymerization ratio are plotted in Example 11.

In the storage unit 100, polymerization conditions were stored in which the slope (polymerization rate) of the polymerization ratio from 10% to 80% was 2.43%/hr (average value) and the standard deviation of the polymerization rate (slope) every hour was 0.67%/hr. The polymerization temperature calculating unit 180 accessed the polymerization conditions stored in the storage unit 100 and calculated the polymerization temperature conditions for each polymerization time. FIG. 8 shows a chart in which polymerization temperature conditions for each polymerization time, a polymerization time, and a polymerization ratio, which are displayed on a monitor (not shown), are plotted.

Example 12

Polymerization was performed under the temperature conditions obtained in Example 11.

507.6 parts by weight of a mixture of 2,5-bis(isothiocyanatomethyl) bicyclo-[2.2.1]-heptane and 2,6-bis(isothiocyanatomethyl) bicyclo-[2.2.1]-heptane were stirred under a nitrogen atmosphere while maintaining the temperature at 15° C. and 3.30 parts by weight of ethylenediamine were dropped therein at a constant rate over 2 hours using a syringe. Thereafter, the mixture was further aged at 15° C. for 1 hour to obtain a reaction solution. To the reaction solution, 0.50 parts by weight of dibutyltin dichloride were added, 2.30 parts by weight of an internal release agent for MR (manufactured by Mitsui Chemicals, Inc.) as an internal release agent were added thereto, and stirring was carried out to dissolve the mixture. To this mixture, 415.4 parts by weight of 4-mercaptomethyl-1,8-dimercapto-3,6-dithiaoctane were further added and mixing and stirring were carried out at 15° C. Thereafter, filtration was carried out to purify the mixture and the solution was depressurized and degassed by a vacuum pump. This solution was cast in a glass mold to create 10 samples. The above was carried out in a mold shape of Φ81 mm, in which the front surface had 2 curves, the back surface had 6 curves, and the center thickness was thick at 15.6 mm.

Polymerization was performed by the apparatus for manufacturing optical material of the present embodiment. The temperature of the polymerization oven was set on the basis of the temperature conditions obtained in Example 11 and the temperature conditions were controlled. After the polymerization was completed (polymerization ratio: 96.9%), a cured polythiourethane resin was obtained from a polymerization oven after cooling. After removing internal stress by an annealing treatment, the obtained resin was evaluated for optical distortion by a high-pressure mercury lamp and, as a result, in 10 out of 10 samples, lenses were obtained which did not have optical distortion and which were extremely excellent for optical applications.

Comparative Example 1

Figure 9:
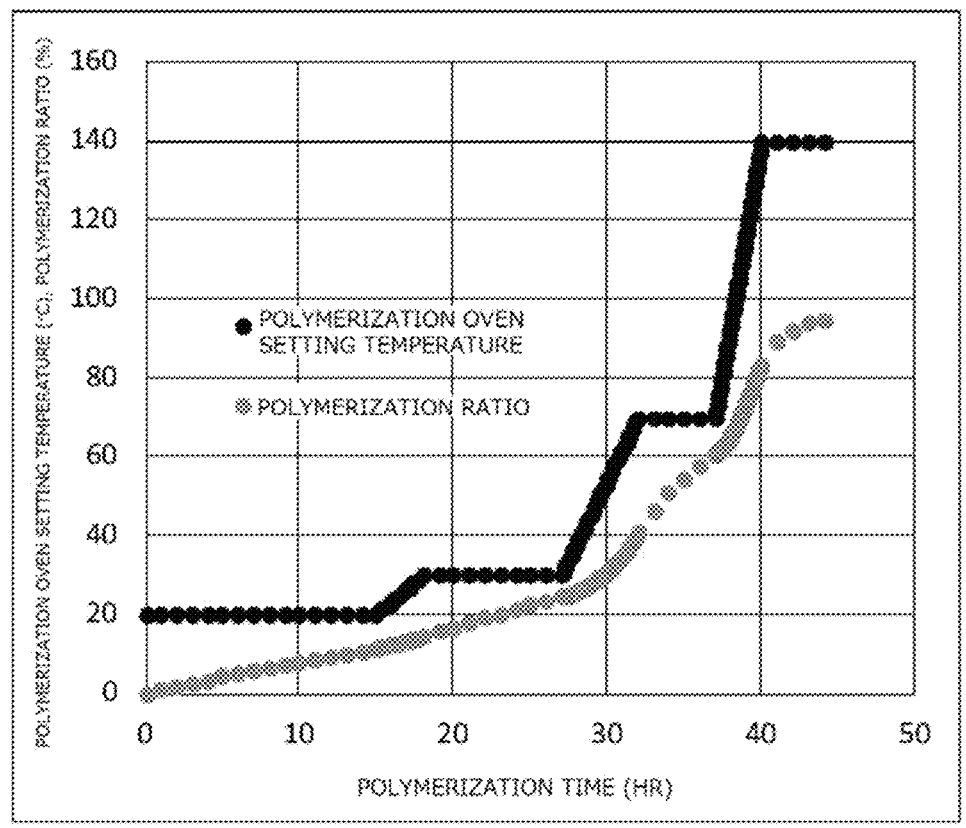
FIG. 9 is a chart in which a polymerization temperature condition for each polymerization time obtained by the method for setting polymerization condition, a polymerization time, and a polymerization ratio are plotted in Comparative Example 1.

The same process as in Example 1 was performed, except that temperature conditions were created where the slope (polymerization rate) of the polymerization ratio from 10% to 80% was 2.65%/hr (average value) and the standard deviation of the polymerization rate (slope) every hour was 2.38%/hr. FIG. 9 shows a chart in which polymerization temperature conditions for each polymerization time, a polymerization time, and a polymerization ratio, which are displayed on a monitor (not shown), are plotted.

Comparative Example 2

Polymerization was performed under the temperature conditions obtained in Comparative Example 1.

To 589 parts by weight of an isocyanate composition (manufactured by Evonic) including dicyclohexylmethane 4,4'-isocyanate, 15 parts by weight of an ultraviolet absorber Eversorb-109, 6.4 parts by weight of Tinuvin-326, and 1.8 parts by weight of dibutyltin dichloride (manufactured by Kyodo Chemical Co., Ltd.) as a catalyst were added, 1.5 parts by weight of an internal release agent for MR (manufactured by Mitsui Chemicals) as an internal release agent were added thereto, and mixing and stirring were carried out at 15° C. to 25° C. to dissolve the mixture. To the mixture, 411 parts by weight of a thiol composition including 5,7-dimercaptomethyl-1,11-dimercapto-3,6,9-trithiaundecane, 4,7-dimercaptomethyl-1,11-dimercapto-3,6,9-trithiaundecane and 4,8-dimercaptomethyl-1,11-dimercapto-3,6,9-trithiaundecane were further added and mixing and stirring were carried out at 15° C. to 25° C. Thereafter, filtration was carried out to purify the mixture and the solution was depressurized and degassed by a vacuum pump. This solution was cast in a glass mold to create 10 samples. The above was carried out in a mold shape of 081 mm, in which the front surface had 2 curves, the back surface had 6 curves, and the center thickness was thick at 15.6 mm.

Polymerization was performed by the apparatus for manufacturing optical material of the present embodiment. The temperature of the polymerization oven was set on the basis of the temperature conditions obtained in Comparative Example 1 and the temperature conditions were controlled. After the polymerization was completed, the mixture was cooled to obtain a cured resin. After removing internal stress by an annealing treatment, the obtained resin was evaluated for optical distortion by a high-pressure mercury lamp and, as a result, in 10 out of 10 samples, optical distortion (striae) was generated and use was not possible as for optical applications.

Comparative Example 3

19.6 parts by weight of m-xylylene diisocyanate, 29.7 parts by weight of an isocyanate composition including 2,5-bis(isothiocyanatomethyl) bicyclo-[2.2.1]-heptane and 2,6-bis(isothiocyanatomethyl) bicyclo-[2.2.1]-heptane, 0.05 parts by weight of Seesorb-701 (manufactured by Shipro Kasei Kaisha, Ltd.) as an ultraviolet absorber, 0.01 parts by weight of dibutyltin dichloride (manufactured by Kyodo Chemical Co., Ltd.), and 0.1 parts by weight of ZelecUN (manufactured by Stepan) as an internal release agent were added, mixed, stirred, and dissolved. To this mixture, 50.7 parts by weight of a polythiol composition including 1,1,3,3-tetrakis (mercaptomethylthio) propane were further added and mixing and stirring were carried out at 15° C. to 25° C. Thereafter, filtration was carried out to purify the mixture and the solution was depressurized and degassed by a vacuum pump. This solution was cast in a glass mold to create 10 samples. The above was carried out in a mold shape of 081 mm, in which the front surface had 2 curves, the back surface had 2 curves, and the center thickness was thick at 15.0 mm.

The same process as in Example 1 was performed, except that temperature conditions were created where the slope (polymerization rate) of the polymerization ratio from 10% to 55% was 1.99%/hr (average value) and the standard deviation of the polymerization rate (slope) every hour was 0.89%/hr.

Polymerization was performed by the apparatus for manufacturing optical material of the present embodiment. After the polymerization, when the mixture was cooled to 60° C. to obtain a resin, the resin was not sufficiently cured and had softness, and use as a lens was not possible.

Comparative Example 4

Figure 10:
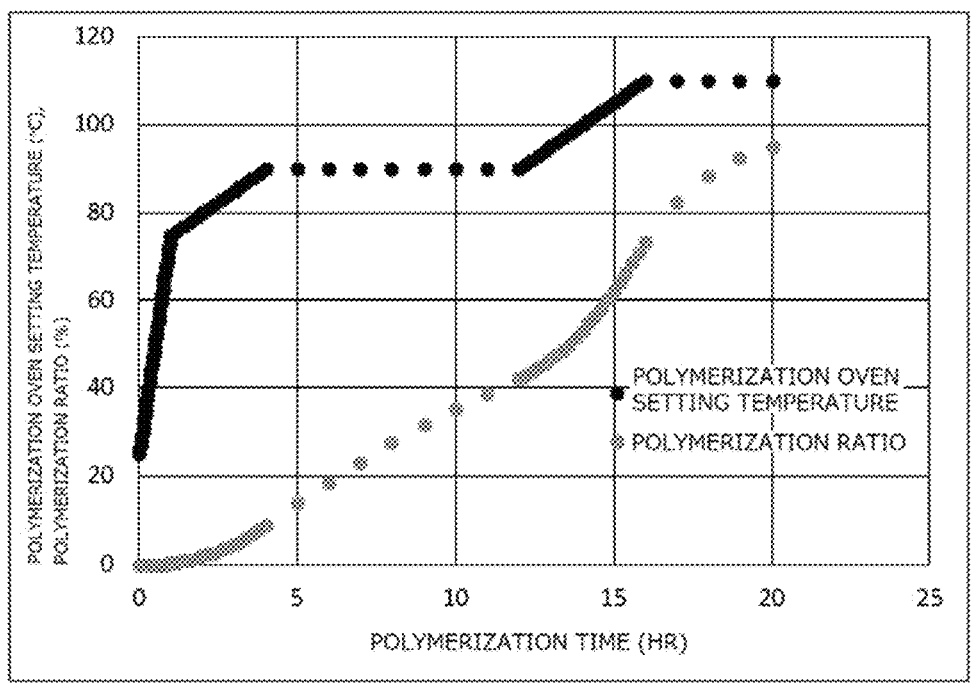
FIG. 10 is a chart in which a polymerization temperature condition for each polymerization time obtained by the method for setting polymerization condition, a polymerization time, and a polymerization ratio are plotted in Comparative Example 4.

The same process as in Example 7 was performed, except that temperature conditions were created where the slope (polymerization rate) of the polymerization ratio from 10% to 80% was 5.57%/hr (average value) and the standard deviation of the polymerization rate (slope) every hour was 2.32%/hr. FIG. 10 shows a chart in which polymerization temperature conditions for each polymerization time, a polymerization time and a polymerization ratio, which are displayed on a monitor (not shown), are plotted.

Comparative Example 5

Polymerization was performed under the temperature conditions obtained in Comparative Example 4.

To 992 parts by weight of RAV 7MC (manufactured by Acomon), 8 parts by weight of Luperox 531M80 (manufactured by ARKEMA Yoshitomi Ltd.) as a radical polymerization initiator and 0.50 parts by weight of polypropylene glycol, diol type, 2000 (manufactured by Wako Pure Chemical Industries, Ltd.) were added, followed by stirring and mixing. The result was purified by filtration, degassed under reduced pressure, and then cast. There were two types of cast mold shapes used and the mold shape 1 was 081 mm, in which the front surface had 2 curves, the back surface had 6 curves, and the center thickness was thick at 10 mm and the mold shape 2 was 081 mm, in which the front surface had 2 curves, the back surface had 6 curves, and the center thickness was thin at 2 mm and 10 samples were cast with each. Polymerization was performed by the apparatus for manufacturing optical material of the present embodiment. The temperature of the polymerization oven was set on the basis of the temperature conditions obtained in Comparative Example 4 and the temperature conditions were controlled. After the polymerization, cooling was carried out to 60° C. and a molded product was released from the mold.

In the lenses molded in mold shape 1, cracks occurred in three of the molded lenses during curing, cracks occurred in five lenses during cooling, and two lenses were obtained as normal cured products.

In the lenses molded in mold shape 2, cracks occurred in five of the molded lenses during curing, cracks occurred in two of the lenses during cooling, and, among the lenses obtained as cured products, three lenses were released too early such that it was not possible to obtain a lens for a normal optical application.

Comparative Example 6

Figure 11:
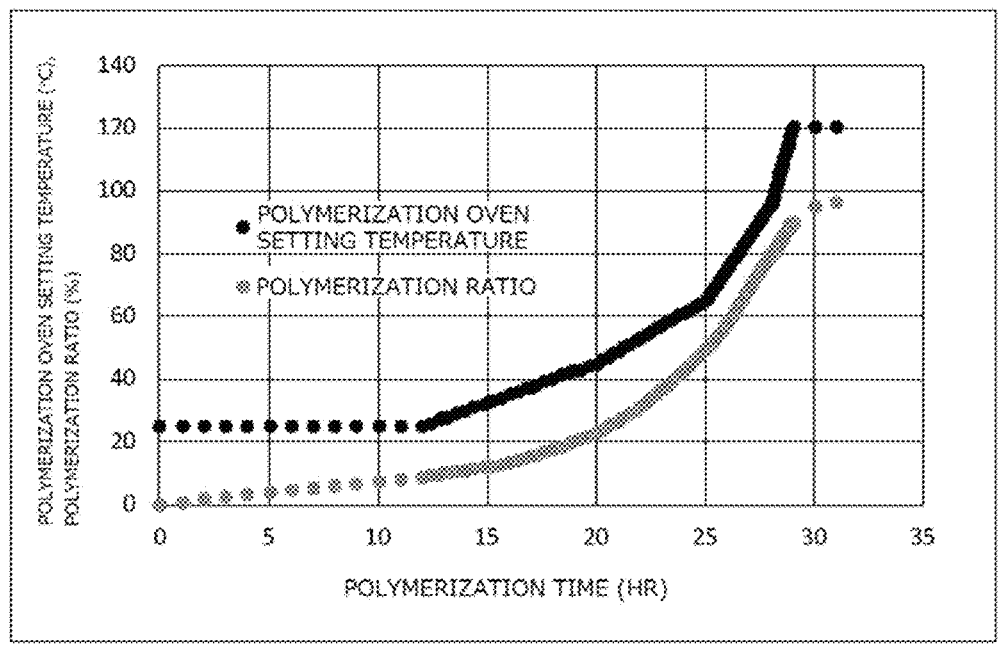
FIG. 11 is a chart in which a polymerization temperature condition for each polymerization time obtained by the method for setting polymerization condition, a polymerization time, and a polymerization ratio are plotted in Comparative Example 6.

The same process as in Example 11 was performed, except that temperature conditions were created where the slope (polymerization rate) of the polymerization ratio from 10% to 80% was 4.38%/hr (average value) and the standard deviation of the polymerization rate (slope) every hour was 3.20%/hr. FIG. 11 shows a chart in which polymerization temperature conditions for each polymerization time, a polymerization time, and a polymerization ratio, which are displayed on a monitor (not shown), are plotted.

Comparative Example 7

Polymerization was performed under the temperature conditions obtained in Comparative Example 6. 507.6 parts by weight of a mixture of 2,5-bis(isothiocyanatomethyl)bicyclo-[2.2.1]-heptane and 2,6-bis(isothiocyanatomethyl)bicyclo-[2.2.1]-heptane were stirred under a nitrogen atmosphere while maintaining the temperature at 15° C. and 3.30 parts by weight of ethylenediamine was dropped therein at a constant rate over 2 hours using a syringe. Thereafter, the mixture was further aged at 15° C. for 1 hour to obtain a reaction solution. To the solution, 0.50 parts by weight of dibutyltin dichloride was added, 2.30 parts by weight of an internal release agent for MR (manufactured by Mitsui Chemicals, Inc.) as an internal release agent were added thereto, stirred, and dissolved. To this mixture, 415.4 parts by weight of 4-mercaptomethyl-1,8-dimercapto-3,6-dithiaoctane were further added and mixing and stirring were carried out at 15° C. Thereafter, filtration was carried out to purify the mixture and the solution was depressurized and degassed by a vacuum pump. This solution was cast in a glass mold to create 10 samples. The above was carried out in a mold shape of Φ81 mm, in which the front surface had 2 curves, the back surface had 6 curves, and the center thickness was thick at 15.6 mm.

Polymerization was performed by the apparatus for manufacturing optical material of the present embodiment. The temperature of the polymerization oven was set on the basis of the temperature conditions obtained in Comparative Example 6 and the temperature conditions were controlled. After the polymerization was completed, the mixture was cooled to obtain a cured resin. After removing internal stress by an annealing treatment, the obtained resin was evaluated for optical distortion by a high-pressure mercury lamp and, as a result, in 10 out of 10 samples, optical distortion (striae) was generated and use was not possible as for optical applications.

This application claims priority based on Japanese Patent Application No. 2018-059326 filed on Mar. 27, 2018, the disclosure of which is incorporated herein in its entirety.

The invention claimed is:

1. A method for manufacturing an optical material, comprising:
a physical property acquiring step comprising:
acquiring a physical property value A derived from a functional group before heating of a composition including a polymerization-reactive compound, a polymerization catalyst, and/or a polymerization initiator,
heating the composition and retaining heat at a plurality of predetermined temperatures, and
acquiring a physical property value B derived from a remaining functional group after maintaining each of the plurality of predetermined temperatures for predetermined times;
a remaining functional group ratio calculating step of calculating a remaining functional group ratio from the physical property value A and the physical property value B;
a reaction rate coefficient calculating step of calculating a reaction rate coefficient from the remaining functional group ratio on the basis of a reaction rate equation;
a polymerization temperature calculating step of back-calculating a plurality of polymerization temperatures at predetermined time intervals within a polymerization time based on the reaction rate equation using the reaction rate coefficient so as to satisfy the following conditions:
selecting and determining an average polymerization rate from a range of 0.4%/hr or more and 15%/hr or less in a range of 10% or more and 80% or less of a conversion ratio,
calculating multiple polymerization rates at predetermined time intervals within the time when the conversion ratio is in the range of 10% or more and 80% or less,
calculating a standard deviation by the positive square root of the variance of the multiple polymerization rates and the average polymerization rate, and
satisfying 2.3%/hr or less of the calculated standard deviation; and
a polymerization step of polymerizing a composition including the polyisocyanate compound, the active hydrogen compound, and the polymerization catalyst and/or the polymerization initiator to satisfy each polymerization temperature at predetermined time intervals obtained in the polymerization temperature calculating step.

2. The method for manufacturing an optical material according to claim 1,
wherein the polyisocyanate compound includes at least one kind selected from an aliphatic polyisocyanate, an aromatic polyisocyanate, a heterocyclic polyisocyanate, and an alicyclic polyisocyanate.

3. The method for manufacturing an optical material according to claim 1,
wherein the active hydrogen compound includes at least one kind selected from a group consisting of a polythiol compound having two or more mercapto groups, a hydroxythiol compound having one or more mercapto groups and one or more hydroxyl groups, a polyol compound having two or more hydroxyl groups, and an amine compound.

4. The method for manufacturing an optical material according to claim 1,
wherein the composition includes at least one kind of compound selected from an allyl carbonate compound, a (meth) acrylate compound, and an episulfide compound.

5. The method for manufacturing an optical material according to claim 4,
wherein the allyl carbonate compound is represented by General Formula (1), $$\text{CH}_2=\text{CH}-\text{CH}_2-\text{O}-\underset{\underset{\text{O}}{\|}}{\text{C}}-\text{O}\!\!\left.\rule{0pt}{2.2ex}\right]_m\!\!R^1 \qquad (1)$$

wherein $R^1$ represents a chained or branched divalent to 20-valent group derived from an aliphatic polyol with 3 to 35 carbon atoms which may include a hetero atom, or a divalent to 20-valent group derived from a cycloaliphatic polyol with 5 to 40 carbon atoms which may include a hetero atom, m represents an integer of 2 to 10, and $R^1$ does not include an allyloxycarbonyl group.

6. The method for manufacturing an optical material according to claim 4,
wherein the (meth) acrylate compound is represented by General Formula (2),

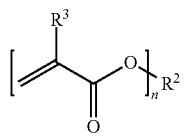

(2)

and wherein $R^2$ represents a divalent to tetravalent organic group with 1 to 30 carbon atoms which may include a hetero atom or an aromatic group, $R^3$ represents a hydrogen atom or a methyl group, and n represents an integer of 2 to 4.

7. The method for manufacturing an optical material according to claim 4,
wherein the episulfide compound is represented by General Formula (3),

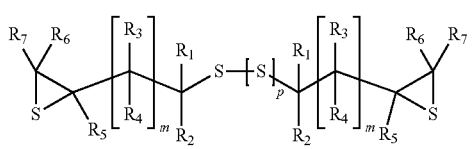

(3)

wherein General Formula (3), $R_1$ to $R_7$ may be the same or different and represent a hydrogen atom, a linear or branched alkyl group with 1 or more and 10 or less carbon atoms, or a substituted or unsubstituted aryl group with 6 or more and 18 or less carbon atoms, m represents an integer of 0 or more and 2 or less, and p represents an integer of 0 or more and 4 or less.

8. The method for manufacturing an optical material according to claim 1,
wherein the physical property values A and B are selected from the group consisting of a heat value, a specific gravity, a weight-average molecular weight, a number-average molecular weight, a spectral intensity in IR measurement, a $^1$H-NMR spectral intensity, and a $^{13}$C-NMR spectral intensity.

9. An apparatus for setting polymerization conditions comprising:
a storage unit;
a memory and instructions stored therein configured to:
acquire, from the storage unit, a physical property value A derived from a functional group before heating of a composition including a polymerization-reactive compound, a polymerization catalyst, and/or a polymerization initiator,
heat the composition and retaining heat at a plurality of predetermined temperatures, and
acquire, from the storage unit, a physical property value B derived from a remaining functional group after maintaining each of the plurality of predetermined temperatures for a predetermined times from a storage; and
a CPU and instructions stored therein configured to:
calculate a remaining functional group ratio from the physical property value A and the physical property value B,
calculate a reaction rate coefficient from the remaining functional group ratio on the basis of a reaction rate equation, and
back-calculate a plurality of polymerization temperatures at predetermined time intervals within a polymerization time based on the reaction rate equation using the reaction rate coefficient so as to satisfy the following conditions:
selecting and determining an average polymerization rate from a range of 0.4%/hr or more and 15%/hr or less in a range of 10% or more and 80% or less of a conversion ratio,
calculating multiple polymerization rates at predetermined time intervals within the time when the conversion ratio is in the range of 10% or more and 80% or less,
calculating a standard deviation by the positive square root of the variance of the multiple polymerization rates and the average polymerization rate, and
satisfying 2.3%/hr or less of the calculated standard deviation.

10. A non-transitory computer readable medium having stored thereon a computer program for setting polymerization conditions for a composition including a polymerization-reactive compound, a polymerization catalyst, and/or a polymerization initiator, the computer program causing a computer to implement functions of:
a storage unit;
a memory and instructions stored therein configured to:
acquire, from the storage unit, a physical property value A derived from a functional group before heating of the composition,
heat the composition and retaining heat at a plurality of predetermined temperatures, and
acquiring, from the storage unit, a physical property value B derived from a remaining functional group after maintaining a each of the plurality of predetermined temperatures for predetermined times; and
a CPU and instructions stored therein configured to:
calculate a remaining functional group ratio from the physical property value A and the physical property value B;
calculate a reaction rate coefficient from the remaining functional group ratio on the basis of a reaction rate equation; and
back-calculate a plurality of polymerization temperatures at predetermined time intervals within a polymerization time based on the reaction rate equation using the reaction rate coefficient so as to satisfy the following conditions:
selecting and determining an average polymerization rate from a range of 0.4%/hr or more and 15%/hr or less in a range of 10% or more and 80% or less of a conversion ratio,
calculating multiple polymerization rates at predetermined time intervals within the time when the conversion ratio is in the range of 10% or more and 80% or less,
calculating a standard deviation by the positive square root of the variance of the multiple polymerization rates and the average polymerization rate, and
satisfying 2.3%/hr or less of the calculated standard deviation.

11. An apparatus for manufacturing optical material comprising:
- a heating furnace for heating a composition including a polymerization-reactive compound and a polymerization catalyst and/or a polymerization initiator;
- an apparatus for setting polymerization conditions comprising:
    - a storage unit,
    - a memory and instructions stored therein configured to:
        - acquire, from the storage unit, a physical property value A derived from a functional group before heating of a composition including a polymerization-reactive compound, a polymerization catalyst, and/or a polymerization initiator,
        - heat the composition and retaining heat at a plurality of predetermined temperatures, and
        - acquire, from the storage unit, a physical property value B derived from a remaining functional group after maintaining each of the plurality of predetermined temperatures for predetermined times from a storage, and a CPU and instructions stored therein configured to:
        - calculate a remaining functional group ratio from the physical property value A and the physical property value B,
        - calculate a reaction rate coefficient from the remaining functional group ratio on the basis of a reaction rate equation, and
        - back-calculate a plurality of polymerization temperatures at predetermined time intervals within a polymerization time based on the reaction rate equation using the reaction rate coefficient so as to satisfy the following conditions:
            - selecting and determining an average polymerization rate from a range of 0.4%/hr or more and 15%/hr or less in a range of 10% or more and 80% or less of a conversion ratio,
            - calculating multiple polymerization rates at predetermined time intervals within the time when the conversion ratio is in the range of 10% or more and 80% or less,
            - calculating a standard deviation by the positive square root of the variance of the multiple polymerization rates and the average polymerization rate, and
            - satisfying 2.3%/hr or less of the calculated standard deviation; and
- wherein the CPU is configured to control the heating furnace so as to heat the composition on the basis of polymerization temperature conditions obtained by the apparatus for setting polymerization conditions.

* * * * *